US006458576B1

United States Patent
Meyers et al.

(10) Patent No.: US 6,458,576 B1
(45) Date of Patent: Oct. 1, 2002

(54) 22406, A NOVEL HUMAN PYRIDOXAL-PHOSPHATE DEPENDENT ENZYME FAMILY MEMBER AND USES THEREFOR

(75) Inventors: Rachel A. Meyers, Newton, MA (US); Laura A. Rudolph-Owen, Jamaica Plain, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/789,300

(22) Filed: Feb. 20, 2001

Related U.S. Application Data

(60) Provisional application No. 60/183,208, filed on Feb. 17, 2000.

(51) Int. Cl.[7] .............................. C12N 9/90; C12N 5/00; C07H 21/04
(52) U.S. Cl. .................. 435/233; 435/325; 435/252.33; 435/320.1; 536/23.2; 536/23.5
(58) Field of Search ................ 435/233, 252.3, 435/252.33, 325, 320.1; 536/23.2, 23.5

(56) References Cited

FOREIGN PATENT DOCUMENTS

WO    WO 00/43526 A1    7/2000

OTHER PUBLICATIONS

Hillier et al. Data Base: EST, Accession No.: H73097, Dated Oct. 31, 1995.*
DeMiranda et al. (2000) "Human Serine Racemase: Moleular Cloning, Genomic Organization and Functional Analysis," *Gene* 256:183–188 (XP004238403).

Wolosker et al. (1999) "Serine Racemase: A Glial Enzyme Synthesizing D–Serine to Regulate Glutamate–N–Methyl–D–Aspartate Neurotransmission," *Proc. Natl. Acad. Sci. USA* 96:13409–13414 (XP002135967).

Database EMBL Online!, Accession No. AA432108, Hillier et al. (1997) "zw89f02.s1 Soares_total_fetus¯Nb2HF8_ 9w Homo sapiens cDNA Image:784155 3' similar to SW:YKV8_Yeast P36007 Hypothetical 34.9 KD protein in FRE2–JEN1 intergenic region.; mRNA sequence," (XP002170836).

Database EMBL Online!, Accession No. AA877666, Submitted Mar. 30, 1998, "nr06b04.s1 NCL¯CGAP_Co10 Homo sapiens cDNA clone Image: 1161007 3', mRNA sequence," (XP002170837).

* cited by examiner

*Primary Examiner*—Nashaat T. Nashed
(74) *Attorney, Agent, or Firm*—Alston & Bird LLP

(57) ABSTRACT

The invention provides isolated nucleic acids molecules, designated 22406 nucleic acid molecules, which encode a novel pyridoxal-phosphate dependent serine racemase. In particular, the invention relates to 22406 serine racemase polypeptide and encoding nucleic acid molecules. The invention also provides antisense nucleic acid molecules, recombinant expression vectors containing 22406 nucleic acid molecules, host cells into which the expression vectors have been introduced, and nonhuman transgenic animals in which a 22406 gene has been introduced or disrupted. The invention still further provides isolated 22406 proteins, fusion proteins, antigenic peptides and anti-22406 antibodies. Diagnostic methods utilizing compositions of the invention are also provided.

8 Claims, 12 Drawing Sheets

```
Input file Fbh22406fl.seq; Output: File 22406.trans
Sequence length 1770
                                                                    M   C       2
CACGCGTCCGGGCCGGGGAGGCGCGCGGAGGCTGGAGCTGGAGGCGCGGCGCCGGTGAGCTGAGAACC ATG TGT   6
 A   Q   Y   C   I   S   F   A   D   V   E   K   A   H   I   N   I   R   D   S  22
GCT CAG TAT TGC ATC TCC TTT GCT GAT GTT GAA AAA GCT CAT ATC AAC ATT CGA GAT TCT  66
 I   H   L   T   P   V   L   T   S   S   I   L   N   Q   L   T   G   R   N   L  42
ATC CAC CTC ACA CCA GTG CTA ACA AGC TCC ATT TTG AAT CAA CTA ACA GGG CGC AAT CTT 126
 F   F   K   C   E   L   F   Q   K   T   G   S   F   K   I   R   G   A   L   N  62
TTC TTC AAA TGT GAA CTC TTC CAG AAA ACA GGA TCT TTT AAG ATT CGT GGT GCT CTC AAT 186
 A   V   R   S   L   V   P   D   A   L   E   R   K   P   K   A   V   V   T   H  82
GCC GTC AGA AGC TTG GTT CCT GAT GCT TTA GAA AGG AAG CCG AAA GCT GTT GTT ACT CAC 246
 S   S   G   N   H   G   Q   A   L   T   Y   A   A   K   L   E   G   I   P   A 102
AGC AGT GGA AAC CAT GGC CAG GCT CTC ACC TAT GCT GCC AAA TTG GAA GGA ATT CCT GCT 306
 Y   I   V   V   P   Q   T   A   P   D   C   K   K   L   A   I   Q   A   Y   G 122
TAT ATT GTG GTG CCC CAG ACA GCT CCA GAC TGT AAA AAA CTT GCA ATA CAA GCC TAC GGA 366
 A   S   I   V   Y   C   E   P   S   D   E   S   R   E   N   V   A   K   R   V 142
GCG TCA ATT GTA TAC TGT GAA CCT AGT GAT GAG TCC AGA GAA AAT GTT GCA AAA AGA GTT 426
 T   E   E   T   E   G   I   M   V   H   P   N   Q   E   P   A   V   I   A   G 162
ACA GAA GAA ACA GAA GGC ATC ATG GTA CAT CCC AAC CAG GAG CCT GCA GTG ATA GCT GGA 486
 Q   G   T   I   A   L   E   V   L   N   Q   V   P   L   V   D   A   L   V   V 182
CAA GGG ACA ATT GCC CTG GAA GTG CTG AAC CAG GTT CCT TTG GTG GAT GCA CTG GTG GTA 546
 P   V   G   G   G   M   L   A   G   I   A   I   T   V   K   A   L   K   P     202
CCT GTA GGT GGA GGA GGA ATG CTT GCT GGA ATA GCA ATT ACA GTT AAG GCT CTG AAA CCT 606
 S   V   K   V   Y   A   A   E   P   S   N   A   D   D   C   Y   Q   S   K   L 222
AGT GTG AAG GTA TAT GCT GCT GAA CCC TCA AAT GCA GAT GAC TGC TAC CAG TCC AAG CTG 666
 K   G   K   L   M   P   N   L   Y   P   P   E   T   I   A   D   G   V   K   S 242
AAG GGG AAA CTG ATG CCC AAT CTT TAT CCT CCA GAA ACC ATA GCA GAT GGT GTC AAA TCC 726
 S   I   G   L   N   T   W   P   I   I   R   D   L   V   D   D   I   F   T   V 262
AGC ATT GGC TTG AAC ACC TGG CCT ATT ATC AGG GAC CTT GTG GAT GAT ATC TTC ACT GTC 786
 T   E   D   E   I   K   C   A   T   Q   L   V   W   E   R   M   K   L   L   I 282
ACA GAG GAT GAA ATT AAG TGT GCA ACC CAG CTG GTG TGG GAG AGG ATG AAA CTA CTC ATT 846
 E   P   T   A   G   V   G   V   A   A   V   L   S   Q   H   F   Q   T   V   S 302
GAA CCT ACA GCT GGT GTT GGA GTG GCT GCT GTG CTG TCT CAA CAT TTT CAA ACT GTT TCC 906
 P   E   V   K   N   I   C   I   V   L   S   G   G   N   V   D   L   T   S   S 322
CCA GAA GTA AAG AAC ATT TGT ATT GTG CTC AGT GGT GGA AAT GTA GAC TTA ACC TCC TCC 966
 I   T   W   V   K   Q   A   E   R   P   A   S   Y   Q   S   V   S   V   *     341
ATA ACT TGG GTG AAG CAG GCT GAA AGG CCA GCT TCT TAT CAG TCT GTT TCT GTT TAA    1023
```

TTTACAGAAAAGGAAATGGTGGGAATTCAGTGTCTTTAGATACTGAAGACATTTTGTTTCCTAGTATTGTCAACTCTTA

GTTATCAGATTCTTAATGGAGAGTGGCTATTTCATTAAGATTTAATAGTTTTTTTTGGACTAAGTAGTGGAAAAACTTT

FIG. 1A.

TATACTTAACTGAGACATTTTGTCAAGGCTAAAAAAAAGTCTTGCAAAATGGGGCAGTGGACTGACAGGCTGACATAGA

AAATAAACTTTGCCCAATCACAACTTGTGCCTCCCATCCCTGGAGTACTGACTGGCACCGGTAAGACAGAATCTCTTTG

AATCCATTACTCCATGCCCCCTTGAGGCACTGTTGAAGAAATCTCACTTTTCAGCCAGGGTACTGGTTCTGGTACATAT

GGATCATAAGTCCATTTGGGGAAGACTCGTTTATACAGGTTCATCAGTACTGTGTCTTGAGATTTTAGCTTCCCATCAA

AGCTGCATTTCATGTGGCCATGGGTACCTAGAAAGACATCAGAACAAGTCGGTCAAATTAAAAGTAGAAAATTTTAAAG

CAATGACTTCCAACCCAACAGTCATTTAGCAACACTGCAGAAATGCAGACATGGTCTCAAATCCCGTGTTTCCTTACCT

AAAGGTTCCTTGATATGTCCTCTCCGGCCCCCACTTCGTTCTCAGTT

FIG. 1B.

Transmembrane Segments Predicted by MEMSAT

Analysis of 22406

| Start | End | Orient | Score |
|-------|-----|--------|-------|
| 176 | 197 | ins–>out | 2.6 |
| 308 | 326 | out–>ins | 0.4 |

```
>22406
MCAQYCISFADVEKAHINIRDSIHLTPVLTSSILNQLTGRNLFFKCELFQKTGSFKIRGA
LNAVRSLVPDALERKPKAVVTHSSGNHGQALTYAAKLEGIPAYIVVPQTAPDCKKLAIQA
YGASIVYCEPSDESRENVAKRVTEETEGIMVHPNQEPAVIAGQGTIALEVLNQVPLVDAL
VVPVGGGGHLAGIAITVKALKPSVKVYAAEPSNADDCYQSKLKGLMPNLYPPETIADGV
KSSIGLNTWPIIRDLVDDIFTVTEDEIKCATQLVWERMKLLIEPTAGVGVAAVLSQHFQT
VSPEVKNICIVLSGGNVDLTSSITWVKQAERPASYQSVSV
```

Prosite Pattern Matches for 22406
Prosite version: Release 12.2 of February 1995

>PS00004/PDOC00004/CAMP_PHOSPHO_SITE cAMP- and cGMP-dependent protein kinase phosphorylation site.

Query: 140   KRVT   143

>PS00005/PDOC00005/PKC_PHOSPHO_SITE Protein kinase C phosphorylation site.

Query: 38    TGR    40
Query: 54    SFK    56
Query: 196   TVK    198
Query: 203   SVK    205

>PS00006/PDOC00006/CK2_PHOSPHO_SITE Casein kinase II phosphorylation site.

Query: 8     SFAD   11
Query: 109   TAPD   112
Query: 212   SNAD   215
Query: 235   TIAD   238
Query: 261   TVTE   264

>PS00008/PDOC00008/MYRISTYL N-myristoylation site.

Query: 59    GALNAV  64
Query: 88    GQALTY  93
Query: 187   GGMLAG  192
Query: 239   GVKSSI  244
Query: 287   GVGVAA  292

>PS00165/PDOC00149/DEHYDRATASE_SER_THR Serine/threonine dehydratases pyridoxal-phosphate attachment site.

Query: 47    ELFQKTGSFKIRGA  60

FIG. 4.

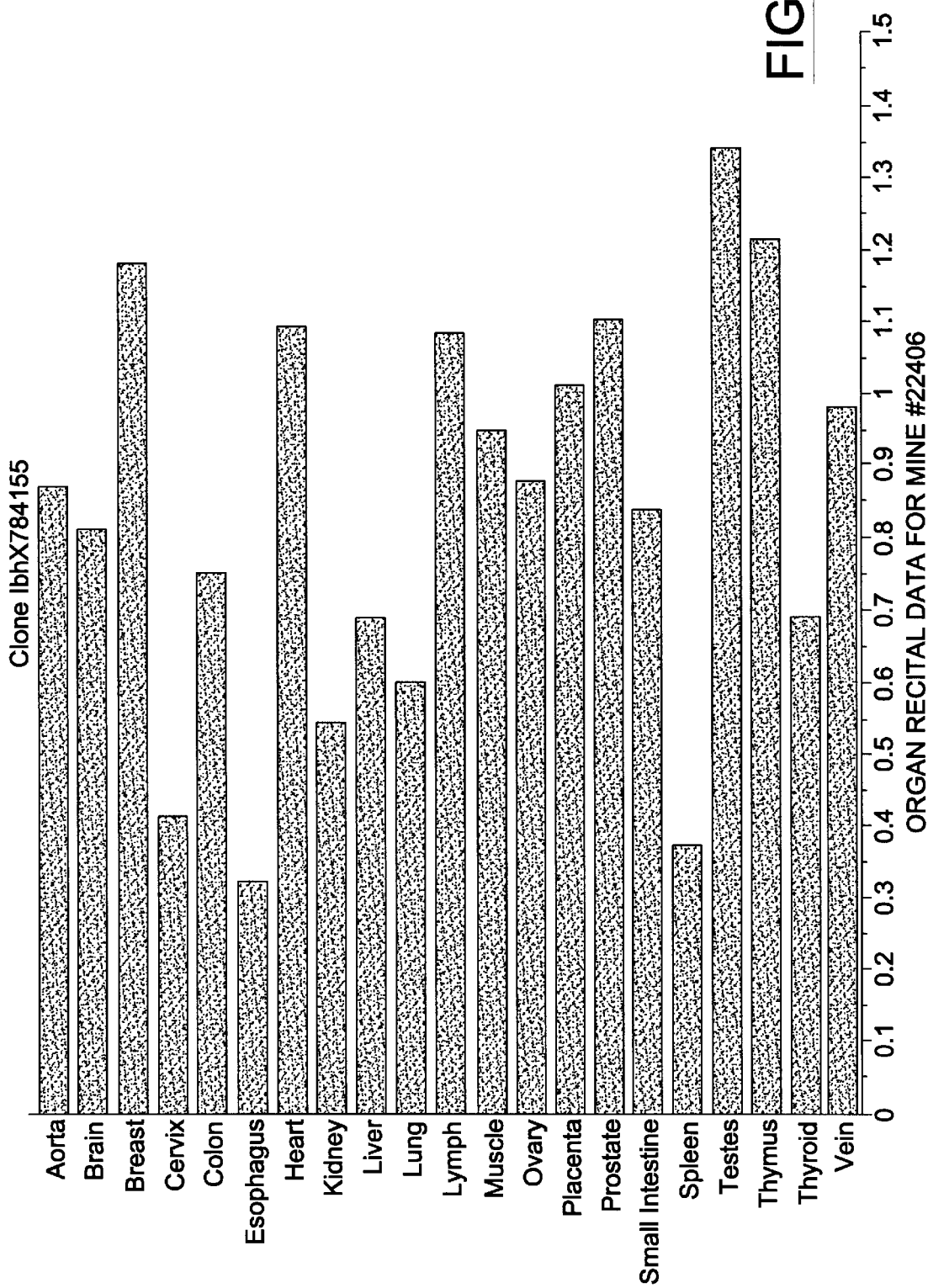

PSORT Prediction of Protein Localization

MITDISC: discrimination of mitochondrial targeting seq
    R content:          0         Hyd Moment (75):   6.24
    Hyd Moment (95):   3.23     G content:        0
    D/E content:       2         S/T content:      1
    Score: -7.07

Gavel: prediction of cleavage sites for mitochondrial preseq
    cleavage site motif not found NUCDISC: discrimination of nuclear localization signals
    pat4: RKPK (4) at 74
    pat7: none
    bipartite: none
    content of basic residues: 9.1%
    NLS Score: -0.22

Final Results (k = 9/23):

34.8%: nuclear
        21.7%: mitochondrial
        21.7%: cytoplasmic
         8.7%: vesicles of secretory system
         4.3%: vacuolar
         4.3%: peroxisomal
         4.3%: endoplasmic reticulum prediction for 22406 is nuc (k=23)

| Start | End | Feature | Seq |
|---|---|---|---|
| 280 | 281 | Dileucine motif in the tail | LL |

FIG. 6.

Protein Family / Domain Matches, HMMer version 2
Searching for complete domains in PFAM
hmmpfam - search a single seq against HMM database
HMMER 2.1.1 (Dec 1998)
Copyright (c) 1992-1998 Washington University School of Medicine
HMMER is freely distributed under the GNU General Public License (GPL).

HMM file: /prod/ddm/seqanal/PFAM/pfam4.4/Pfam
Sequence file: /prod/ddm/wspace/orfanal/oa-script.20753.seq Query: 22406

Scores for sequence family classification (score includes all domains):

| Model | Description | Score | E-value | N |
|---|---|---|---|---|
| S_T_dehydratase | Pyridoxal-phosphate dependent enzyme | 220.9 | 1.8e-62 | 1 |

Parsed for domains:

| Model | Domain | seq-f | seq-t | hmm-f | hmm-t | score | E-value |
|---|---|---|---|---|---|---|---|
| S_T_dehydratase | 1/1 | 19 | 315 .. | 1 | 378 [] | 220.9 | 1.8e-62 |

Alignments of top-scoring domains:
S_T_dehydratase: domain 1 of 1, from 19 to 315: score 220.9, E = 1.8e-62

```
              *->vteligyTPLvr2nr2skelgeglganaaveiy1KlEdlnGPtGSfK
                 +++ l  TP+ ++ l       +g       ++++K+E+++ tGSfK
     22406  19   IRDSIHLTPVLTSSILN----QLTGR----NLFFKCELFQ-KTGSFK 56

DRglalnmil....lAeklgkkgglvpgtvqvesktttiiEptsGNtGial
              +Rg aln++++    ++A +    k++++ +           sGN+G+al
     22406  57 IRG-ALNAVRslvpDALERKPKAVVTHS-------------SGNHGQAL 91

AlaaallGlkctivMPatdtsreKraqlralGAelvvvpvagGgsddlad
              +aa+l G++++iv+P t ++   K+ ++ a+GA +v +++++   s
     22406  92 TYAAKLEGIPAYIVVPQT-APDCKKLAIQAYGASIVYCEPSD-ESRE--- 136 aiakAeelaeenpenayllnqaaGpfdnPanpeiaggktigpEIweQlgg
              +ak +  ee++  +++++     + Pa+++   gq+ti++E++  Q++
     22406 137 NVAK--RVTEETE--GIMVHP----NQEPAVIA--GQGTIALEVLNQVP- 175 keislgrlpDavvapvGgGGtitGiarylKelnpdgkIdvlelpvkvigV
                 l+Da+v+pvGgGG ++Gia    K l+p+       vkv+++
     22406 176 -------LVDALVVPVGGGGMLAGIAITVKALKPS---------VKVYAA 209

EPegsavlsgslkatltlagkpGplhgrdskyllQDepvtlpetksigiG
              EP +++ ++s        +G+l +           l+++ +i++G
     22406 210 EPSNADDCYQSKL--------KGKLMP---------NLYPPETIADG 239 lgvprvgefvppildellorrqgidevvtvtdeealeaarlLarEGilv
              +  + +g  ++pi++ l+d    ++ tvt++e+ a++l++++++++l+
     22406 240 VKSS-IGLNTWPIIRDLVD------DIFTVTEDEIKCATQLVWERMKLLI 282 gpssgaavaaalklakegkkplnkgktiVvilsgg<-*
              +p  g+ vaa+l+  ++ +    ++l+o ++lsgg
     22406 283 EPTAGVGVAAVLSQHFQTV--SPEVKNICIVLSGG 315
```

FROM FIG. 7A.

```
//
Searching for complete domains in SMART
hmmpfam - search a single seq against HMM database
HMMER 2.1.1 (Dec 1998).
Copyright (C) 1992-1998 Washington University School of Medicine
HMMER is freely distributed under the GNU General Public License (GPL).
-----------------------------------------------------------------------
HMM file:              /ddm/robison/smart/smart/smart.all.hmms
Sequence file:         /prod/ddm/wspace/orfanal/oa-script.20753.seq
-----------------------------------------------------------------------
 Query:  22406
Scores for sequence family classification (score includes all domains):
Model   Description                             Score    E-value  N
------  -----------                             -----    -------  ---
        (no hits above thresholds)

Parsed for domains:
Model   Domain  seq-f seq-t    hmm-f hmm-t     score   E-value
------  ------  ----- -----    ----- -----     -----   -------
        (no hits above thresholds)

Alignments of top-scoring domains:
        (no hits above thresholds)
//
```

FIG. 7B.

| ProdomId | Start | End | Description | Score |
|---|---|---|---|---|
| View Prodom 206 | 19 | 316 | p99.2(175) TRPB(29) CYSK(16) THRC(15)//LYASE SYNTHASE PYRIDOXAL PHOSPHATE BIOSYNTHESIS TRYPTOPHAN CYSTEINE THREONINE BETA CHAIN | 103 |
| ProdomId | Start | End | Description | Score |

View Prodom 206
06 p99.2 (175) TRPB(29) CYSK(16) THRC(15) //LYASE SNYTHASE PYRIDOXAL
PHOSPHATE BIOSYNTHESIS TRYPTOPHAN CYSTEINE THREONINE BETA CHAIN
        Length = 374
    Score = 103 (41.3 bits), Expect = 0.0046, Sum P(2) = 0.0046
    Identities = 41/141 (29%), Positives = 69/141 (48%)

```
Query:   19 IRDSIHLTPVLTSSILNQLTGRN--LFFKCE-LFQKTGS--FKIRGALNAVRSLVPDALE 73
            + + I  TP++  + L++ G    ++ K E L    TGS  +k RGA + +    + L
Sbjct:   10 VTELIGNTPLVRLNNLSERLGCKAAIYLKKEELMNPTGSGSYKDRGAYSMISEAEEEGLI 69

Query:   74 R--KPKAVVTHSSGNHGQ-ALTYAAKLEGIPAYIVVPQT-APDCKKLA-IQAYGASIVYC 128
              +   K  +V +SGN G  AL A   G+   IV+P++ + + K+++ ++AYGA IV
Sbjct:   70 KPGKKSVIVESTSGNTGAVALAMVAARLGLKCVIVMPESMSQEQKRVSMLRAYGAEIVLT 129

Query:  129 EPSD--ESRENVAKRVTEEETE 147
              S   E +N     E E
Sbjct:  130 PTSGVVEGSKNYVDAANEAME 150
```

Score = 81 (33.6 bits), Expect = 1.5, P = 0.78
    Identities = 31/101 (30%), Positives = 49/101 (48%)

```
Query:  127 YCEPSDESREN-VAKRVTEETE-GIMVHPNQEPAVIAG----QGTIALEVLNQV------ 174
            Y + ++E+ E+ V+    T  + G V+P+Q P     G     Q T+ E   Q+
Sbjct:  141 YVDAANEAMEDWVSNEETPNSALGTYVNPHQFPNPANGKAHYQTTVPEEWKEQMGEEKEG 200

Query:  175 PLVDALVVPVGGGGMLAGIAITVKAL-KPSVKVYAAEPSNA 214
            VD +V VG GG +AG+A +K    P+VK+   EP +
Sbjct:  201 KKVDVIVASVGTGGTIAGVARYLKLEDNPNVKLVGVEPEGS 241
```

Score = 40 (19.1 bits), Expect = 0.0046, Sum P(2) = 0.0046
    Identities = 26/132 (19%), Positives = 53/132 (40%)

```
Query:  190 LAGIAITVKALKPSVKVYAAEPSNADDCYQSKLKGKLMPN-LYPPETIADGVKSSI-GLN 247
            L G+           ++   ++  E   A   + +    GK+ P+ +     T+A     G
Sbjct:  233 LVGVEPEGGVIETPKRLAGVEAGGAGSLHGALKSGKMQPHKIQGVGTVAVPANLDYPGEV 292

Query:  248 TWPIIRDLVD--DIFTVTEDEIKCATQLVWERMKLLIEPTAGVGVAAVLSQHFQTVSPEV 305
            +I+   D +   +V+++E    A   + E   ++ EP + +AA              +
Sbjct:  293 VDEVIQVSSDRAEEAVSVSDEEALEAGLLLGESEGIVPEPASAAAIAAAKKLAENEGKKDQ 352

Query:  306 KNICIVL-SGGN 316
             I +V+ SGG+
Sbjct:  353 GEIVVVIPSGGD 364
```

FIG. 8.

FROM FIG. 9A.

SEQUENCE LISTING

<160> NUMBER OF SEQ ID NOS: 4

<210> SEQ ID NO 1
<211> LENGTH: 1770
<212> TYPE: DNA
<213> ORGANISM: Homo sapiens
<220> FEATURE:
<221> NAME/KEY: CDS
<222> LOCATION: (69)...(1091)

-continued

```
<400> SEQUENCE: 1
cacgcgtccg ggccggggag gcgcgcggag gctggagctg gaggcgcggc gccggtgagc      60 tgagaacc atg tgt gct cag tat tgc atc tcc ttt gct gat gtt gaa aaa     110
         Met Cys Ala Gln Tyr Cys Ile Ser Phe Ala Asp Val Glu Lys
          1               5                  10 gct cat atc aac att cga gat tct atc cac ctc aca cca gtg cta aca      158
Ala His Ile Asn Ile Arg Asp Ser Ile His Leu Thr Pro Val Leu Thr
 15                  20                  25                  30 agc tcc att ttg aat caa cta aca ggg cgc aat ctt ttc ttc aaa tgt      206
Ser Ser Ile Leu Asn Gln Leu Thr Gly Arg Asn Leu Phe Phe Lys Cys
                 35                  40                  45 gaa ctc ttc cag aaa aca gga tct ttt aag att cgt ggt gct ctc aat      254
Glu Leu Phe Gln Lys Thr Gly Ser Phe Lys Ile Arg Gly Ala Leu Asn
             50                  55                  60 gcc gtc aga agc ttg gtt cct gat gct tta gaa agg aag ccg aaa gct      302
Ala Val Arg Ser Leu Val Pro Asp Ala Leu Glu Arg Lys Pro Lys Ala
         65                  70                  75 gtt gtt act cac agc agt gga aac cat ggc cag gct ctc acc tat gct      350
Val Val Thr His Ser Ser Gly Asn His Gly Gln Ala Leu Thr Tyr Ala
     80                  85                  90 gcc aaa ttg gaa gga att cct gct tat att gtg gtg ccc cag aca gct      398
Ala Lys Leu Glu Gly Ile Pro Ala Tyr Ile Val Val Pro Gln Thr Ala
 95                 100                 105                 110 cca gac tgt aaa aaa ctt gca ata caa gcc tac gga gcg tca att gta      446
Pro Asp Cys Lys Lys Leu Ala Ile Gln Ala Tyr Gly Ala Ser Ile Val
                115                 120                 125 tac tgt gaa cct agt gat gag tcc aga gaa aat gtt gca aaa aga gtt      494
Tyr Cys Glu Pro Ser Asp Glu Ser Arg Glu Asn Val Ala Lys Arg Val
            130                 135                 140 aca gaa gaa aca gaa ggc atc atg gta cat ccc aac cag gag cct gca      542
Thr Glu Glu Thr Glu Gly Ile Met Val His Pro Asn Gln Glu Pro Ala
        145                 150                 155 gtg ata gct gga caa ggg aca att gcc ctg gaa gtg ctg aac cag gtt      590
Val Ile Ala Gly Gln Gly Thr Ile Ala Leu Glu Val Leu Asn Gln Val
    160                 165                 170 cct ttg gtg gat gca ctg gtg gta cct gta ggt gga gga gga atg ctt      638
Pro Leu Val Asp Ala Leu Val Val Pro Val Gly Gly Gly Gly Met Leu
175                 180                 185                 190 gct gga ata gca att aca gtt aag gct ctg aaa cct agt gtg aag gta      686
Ala Gly Ile Ala Ile Thr Val Lys Ala Leu Lys Pro Ser Val Lys Val
                195                 200                 205 tat gct gct gaa ccc tca aat gca gat gac tgc tac cag tcc aag ctg      734
Tyr Ala Ala Glu Pro Ser Asn Ala Asp Asp Cys Tyr Gln Ser Lys Leu
            210                 215                 220 aag ggg aaa ctg atg ccc aat ctt tat cct cca gaa acc ata gca gat      782
Lys Gly Lys Leu Met Pro Asn Leu Tyr Pro Pro Glu Thr Ile Ala Asp
        225                 230                 235 ggt gtc aaa tcc agc att ggc ttg aac acc tgg cct att atc agg gac      830
Gly Val Lys Ser Ser Ile Gly Leu Asn Thr Trp Pro Ile Ile Arg Asp
    240                 245                 250 ctt gtg gat gat atc ttc act gtc aca gag gat gaa att aag tgt gca      878
Leu Val Asp Asp Ile Phe Thr Val Thr Glu Asp Glu Ile Lys Cys Ala
255                 260                 265                 270 acc cag ctg gtg tgg gag agg atg aaa cta ctc att gaa cct aca gct      926
Thr Gln Leu Val Trp Glu Arg Met Lys Leu Leu Ile Glu Pro Thr Ala
                275                 280                 285 ggt gtt gga gtg gct gct gtg ctg tct caa cat ttt caa act gtt tcc      974
Gly Val Gly Val Ala Ala Val Leu Ser Gln His Phe Gln Thr Val Ser
```

-continued

```
              290                 295                 300
cca gaa gta aag aac att tgt att gtg ctc agt ggt gga aat gta gac    1022
Pro Glu Val Lys Asn Ile Cys Ile Val Leu Ser Gly Gly Asn Val Asp
        305                 310                 315 tta acc tcc tcc ata act tgg gtg aag cag gct gaa agg cca gct tct    1070
Leu Thr Ser Ser Ile Thr Trp Val Lys Gln Ala Glu Arg Pro Ala Ser
    320                 325                 330 tat cag tct gtt tct gtt taa tttacagaaa aggaaatggt gggaattcag       1121
Tyr Gln Ser Val Ser Val  *
335                 340 tgtctttaga tactgaagac attttgtttc ctagtattgt caactcttag ttatcagatt  1181
cttaatggag agtggctatt tcattaagat ttaatagttt tttttggact aagtagtgga  1241
aaaactttta tacttaactg agacattttg tcaaggctaa aaaaaagtct tgcaaaatgg  1301
ggcagtggac tgacaggctg acatagaaaa taaactttgc ccaatcacaa cttgtgcctc  1361
ccatccctgg agtactgact ggcaccggta agacagaatc tctttgaatc cattactcca  1421 tgccccttg aggcactgtt gaagaaatct cacttttcag ccagggtact ggttctggta   1481
catatggatc ataagtccat tgggggaaga ctcgtttata caggttcatc agtactgtgt  1541
cttgagattt tagcttccca tcaaagctgc atttcatgtg gccatgggta cctagaaaga  1601
catcagaaca agtcggtcaa attaaaagta gaaaatttta aagcaatgac ttccaaccca  1661
acagtcattt agcaacactg cagaaatgca gacatggtct caaatcccgt gtttccttac  1721
ctaaaggttc cttgatatgt cctctccggc ccccacttcg ttctcagtt              1770

<210> SEQ ID NO 2
<211> LENGTH: 340
<212> TYPE: PRT
<213> ORGANISM: Homo sapiens

<400> SEQUENCE: 2

Met Cys Ala Gln Tyr Cys Ile Ser Phe Ala Asp Val Glu Lys Ala His
 1               5                  10                  15

Ile Asn Ile Arg Asp Ser Ile His Leu Thr Pro Val Leu Thr Ser Ser
            20                  25                  30

Ile Leu Asn Gln Leu Thr Gly Arg Asn Leu Phe Phe Lys Cys Glu Leu
        35                  40                  45

Phe Gln Lys Thr Gly Ser Phe Lys Ile Arg Gly Ala Leu Asn Ala Val
    50                  55                  60

Arg Ser Leu Val Pro Asp Ala Leu Glu Arg Lys Pro Lys Ala Val Val
65                  70                  75                  80

Thr His Ser Ser Gly Asn His Gly Gln Ala Leu Thr Tyr Ala Ala Lys
                85                  90                  95

Leu Glu Gly Ile Pro Ala Tyr Ile Val Val Pro Gln Thr Ala Pro Asp
            100                 105                 110

Cys Lys Lys Leu Ala Ile Gln Ala Tyr Gly Ala Ser Ile Val Tyr Cys
        115                 120                 125

Glu Pro Ser Asp Glu Ser Arg Glu Asn Val Ala Lys Arg Val Thr Glu
    130                 135                 140

Glu Thr Glu Gly Ile Met Val His Pro Asn Gln Glu Pro Ala Val Ile
145                 150                 155                 160

Ala Gly Gln Gly Thr Ile Ala Leu Glu Val Leu Asn Gln Val Pro Leu
                165                 170                 175

Val Asp Ala Leu Val Val Pro Val Gly Gly Gly Met Leu Ala Gly
            180                 185                 190
```

Ile Ala Ile Thr Val Lys Ala Leu Lys Pro Ser Val Lys Val Tyr Ala
        195                 200                 205

Ala Glu Pro Ser Asn Ala Asp Asp Cys Tyr Gln Ser Lys Leu Lys Gly
210                 215                 220

Lys Leu Met Pro Asn Leu Tyr Pro Pro Glu Thr Ile Ala Asp Gly Val
225                 230                 235                 240

Lys Ser Ser Ile Gly Leu Asn Thr Trp Pro Ile Ile Arg Asp Leu Val
                245                 250                 255

Asp Asp Ile Phe Thr Val Thr Glu Asp Glu Ile Lys Cys Ala Thr Gln
            260                 265                 270

Leu Val Trp Glu Arg Met Lys Leu Leu Ile Glu Pro Thr Ala Gly Val
        275                 280                 285

Gly Val Ala Val Leu Ser Gln His Phe Gln Thr Val Ser Pro Glu
    290                 295                 300

Val Lys Asn Ile Cys Ile Val Leu Ser Gly Gly Asn Val Asp Leu Thr
305                 310                 315                 320

Ser Ser Ile Thr Trp Val Lys Gln Ala Glu Arg Pro Ala Ser Tyr Gln
                325                 330                 335

Ser Val Ser Val
        340

<210> SEQ ID NO 3
<211> LENGTH: 1020
<212> TYPE: DNA
<213> ORGANISM: Homo sapiens

<400> SEQUENCE: 3
atgtgtgctc agtattgcat ctcctttgct gatgttgaaa aagctcatat caacattcga      60
gattctatcc acctcacacc agtgctaaca agctccattt tgaatcaact aacagggcgc     120
aatcttttct tcaaatgtga actcttccag aaaacaggat cttttaagat tcgtggtgct     180
ctcaatgccg tcagaagctt ggttcctgat gctttagaaa ggaagccgaa agctgttgtt     240
actcacagca gtggaaaacca tggccaggct ctcacctatg ctgccaaatt ggaaggaatt     300
cctgcttata ttgtggtgcc ccagacagct ccagactgta aaaaacttgc aatacaagcc     360
tacggagcgt caattgtata ctgtgaacct agtgatgagt ccagagaaaa tgttgcaaaa     420
agagttacag aagaaacaga aggcatcatg gtacatccca accaggagcc tgcagtgata     480
gctggacaag ggacaattgc cctggaagtg ctgaaccagg ttcctttggt ggatgcactg     540
gtggtacctg taggtggagg aggaatgctt gctggaatag caattacagt taaggctctg     600
aaacctagtg tgaaggtata tgctgctgaa ccctcaaatg cagatgactg ctaccagtcc     660
aagctgaagg ggaaactgat gcccaatctt tatcctccag aaaccatagc agatggtgtc     720
aaatccagca ttggcttgaa cacctggcct attatcaggg accttgtgga tgatatcttc     780
actgtcacag aggatgaaat taagtgtgca cccagctgg tgtgggagag atgaaacta     840 ctcattgaac ctacagctgg tgttggagtg gctgctgtgc tgtctcaaca ttttcaaact     900
gtttccccag aagtaaagaa catttgtatt gtgctcagtg gtggaaatgt agacttaacc     960
tcctccataa cttgggtgaa gcaggctgaa aggccagctt cttatcagtc tgtttctgtt    1020

<210> SEQ ID NO 4
<211> LENGTH: 378
<212> TYPE: PRT
<213> ORGANISM: Artificial Sequence
<220> FEATURE:

<223> OTHER INFORMATION: Pyridoxal-Phosphate Dependent Enzyme Family Domain Sequence

<400> SEQUENCE: 4

```
Val Thr Glu Leu Ile Gly Asn Thr Pro Leu Val Arg Leu Asn Arg Leu
 1               5                  10                  15
Ser Lys Glu Leu Gly Glu Gly Leu Gly Ala Asn Ala Ala Val Glu Ile
            20                  25                  30
Tyr Leu Lys Leu Glu Asp Leu Asn Gly Pro Thr Gly Ser Phe Lys Asp
        35                  40                  45
Arg Gly Leu Ala Leu Asn Met Ile Leu Ala Glu Lys Leu Gly Lys
50                  55                  60
Lys Gly Gly Ile Val Pro Gly Thr Val Gln Val Glu Ser Lys Thr Thr
65                  70                  75                  80
Ile Ile Glu Pro Thr Ser Gly Asn Thr Gly Ile Ala Leu Ala Leu Ala
                85                  90                  95
Ala Ala Leu Leu Gly Leu Lys Cys Thr Ile Val Met Pro Ala Thr Asp
            100                 105                 110
Thr Ser Arg Glu Lys Arg Ala Gln Leu Arg Ala Leu Gly Ala Glu Leu
        115                 120                 125
Val Val Val Pro Val Ala Gly Gly Ser Asp Asp Leu Ala Asp Ala
130                 135                 140
Ile Ala Lys Ala Glu Glu Leu Ala Glu Glu Asn Pro Glu Asn Ala Tyr
145                 150                 155                 160
Leu Leu Asn Gln Ala Ala Gly Pro Phe Asp Asn Pro Ala Asn Pro Glu
                165                 170                 175
Ile Ala Gly Gln Lys Thr Ile Gly Pro Glu Ile Trp Glu Gln Leu Gly
            180                 185                 190
Gly Lys Glu Ile Ser Leu Gly Arg Leu Pro Asp Ala Val Val Ala Pro
        195                 200                 205
Val Gly Gly Gly Gly Thr Ile Thr Gly Ile Ala Arg Tyr Leu Lys Glu
210                 215                 220
Leu Asn Pro Asp Gly Lys Ile Asp Val Leu Glu Leu Pro Val Lys Val
225                 230                 235                 240
Ile Gly Val Glu Pro Glu Gly Ser Ala Val Leu Ser Gly Ser Leu Lys
                245                 250                 255
Ala Thr Leu Thr Leu Ala Gly Lys Pro Gly Pro Leu His Gly Arg Asp
            260                 265                 270
Ser Lys Tyr Leu Leu Gln Asp Glu Pro Val Thr Leu Pro Glu Thr Lys
        275                 280                 285
Ser Ile Gly Ile Gly Leu Gly Val Pro Arg Val Gly Glu Phe Val Pro
290                 295                 300
Pro Ile Leu Asp Glu Leu Leu Asp Arg Arg Gln Gly Ile Asp Glu Val
305                 310                 315                 320
Val Thr Val Thr Asp Glu Glu Ala Leu Glu Ala Ala Arg Leu Leu Ala
                325                 330                 335
Arg Glu Glu Gly Ile Leu Val Gly Pro Ser Ser Gly Ala Ala Val Ala
            340                 345                 350
Ala Ala Leu Lys Leu Ala Lys Glu Gly Lys Lys Pro Leu Asn Lys Gly
        355                 360                 365
Lys Thr Ile Val Val Ile Leu Ser Gly Gly
370                 375
```

22406, A NOVEL HUMAN PYRIDOXAL-PHOSPHATE DEPENDENT ENZYME FAMILY MEMBER AND USES THEREFOR

CROSS-REFERENCE TO RELATED APPLICATIONS

This application claims the benefit of U.S. Provisional Application No. 60/183,208, filed Feb. 17, 2000, which is hereby incorporated herein in its entirety by reference.

FIELD OF THE INVENTION

The present invention relates to a newly identified protein, 22406, a human pyridoxal-phosphate dependent enzyme family member. In particular, the invention relates to the 22406 polypeptide and encoding nucleic acid molecules, methods of detecting the 22406 polypeptide and encoding nucleic acid molecules, and methods of diagnosing and treating 22406-related disorders. Also provided are vectors, host cells, and recombinant methods for making and using the novel molecules.

BACKGROUND OF THE INVENTION

The pyridoxal-phosphate dependent family of enzymes require the co-factor, pyridoxal-5'-phosphate (pyridoxal-phosphate), for catalytic activity. Pyridoxal-phosphate dependent enzymes (B6 enzymes) catalyze manifold reactions in the metabolism of amino acids. L- and D-serine dehydratase, threonine dehydratase, and serine racemase are a few of the members of this family of enzymes. In all of the members of the family, the pyridoxal-phosphate group is attached to a lysine residue. The sequence around this residue is sufficiently conserved to allow the derivation of a pattern specific to pyridoxal-phosphate dependent enzymes.

The pyridoxal-phosphate dependent family member, serine racemase, has been shown to catalyze the direct racemization of L-serine to D-serine with a requirement for pyridoxal 5'-phosphate (Wolosker et al. (1999) *PNAS* 96:721–725). The properties of this enzyme resemble those of bacterial racemases, suggesting that the biosynthetic pathway for D-amino acids is conserved from bacteria to mammalian brain.

It has been demonstrated that D-serine is the endogenous ligand for the glycine site of the glutamate N-methyl-D-aspartate (NMDA) receptor (Mothet et al. (2000) *PNAS* 97:4926–4931). The amino acid D-serine is synthesized and stored in glia rather than in neurons. Released glutamate acts on receptors on the protoplasmic astrocytes closely opposed to the synapse to release D-serine, which co-activates post-synaptic NMDA receptors together with glutamate. As D-serine is formed by serine racemase, inhibitors of this enzyme can be expected to reduce NMDA neurotransmission.

D-serine has been shown to modify behavioral changes associated with learning, memory, convulsion, anxiety, psychotomimetic induced abnormal behavior, cerebellar ataxia, and neurodengeneration. Inhibitors of serine racemase can be expected to quell anxiety and epilepsy and to prevent damage from stroke and certain neurodegenerative conditions including Alzheimer's disease. On the other hand, stimulating serine racemase might improve schizophrenia symptoms, which are partly caused by depressed NMDA receptor function.

Accordingly, members of the pyridoxal-phosphate dependent enzyme class are a major target for drug action and development. Therefore, it is valuable to the field of pharmaceutical development to identify and characterize previously unknown serine racemases. The present invention advances the state of the art by providing a previously unidentified human pyridoxal-phosphate dependent serine racemace.

SUMMARY OF THE INVENTION

The present invention is based, in part, on the discovery of a novel human pyridoxal-phosphate dependent enzyme family member, referred to herein as "22406". The nucleotide sequence of a cDNA encoding 22406 is shown in SEQ ID NO:1, and the amino acid sequence of a 22466 polypeptide is shown in SEQ ID NO:2. In addition, the nucleotide sequence of the coding region is depicted in SEQ ID NO:3.

Accordingly, in one aspect the invention features a nucleic acid molecule which encodes a 22406 protein or polypeptide, e.g., a biologically active portion of the 22406 protein. In a preferred embodiment, the isolated nucleic acid molecule encodes a polypeptide having the amino acid sequence of SEQ ID NO:2; In other embodiments, the invention provides an isolated 22406 nucleic acid molecule having the nucleotide sequence shown in SEQ ID NO:1 or SEQ ID NO:3. In still other embodiments, the invention provides nucleic acid molecules that are substantially identical (e.g., naturally occurring allelic variants) to the nucleotide sequence shown in SEQ ID NO:1 or SEQ ID NO:3. In other embodiments, the invention provides a nucleic acid molecule which hybridizes under stringent hybridization conditions to a nucleic acid molecule comprising the nucleotide sequence of SEQ ID NO:1 or SEQ ID NO:3, wherein the nucleic acid encodes a full length 22406 protein or an active fragment thereof.

In a related aspect, the invention further provides nucleic acid constructs which include a 22406 nucleic acid molecule described herein. In certain embodiments, the nucleic acid molecules of the invention are operatively linked to native or heterologous regulatory sequences. Also included, are vectors and host cells containing the 22406 nucleic acid molecules of the invention e.g., vectors and host cells suitable for producing 22406 nucleic acid molecules and polypeptides.

In another related aspect, the invention provides nucleic acid fragments suitable as primers or hybridization probes for the detection of 22406-encoding nucleic acids.

In still another related aspect, isolated nucleic acid molecules that are antisense to a 22406 encoding nucleic acid molecule are provided.

In another aspect, the invention features 22406 polypeptides, and biologically active or antigenic fragments thereof that are useful, e.g., as reagents or targets in assays applicable to treatment and diagnosis of 22406-mediated or -related disorders. In another embodiment, the invention provides 22406 polypeptides having a 22406 activity. Preferred polypeptides are 22406 proteins including at least one pyridoxal-phosphate dependent enzyme family member domain, and, preferably, having a 22406 activity, e.g., a 22406 activity as described herein.

In other embodiments, the invention provides 22406 polypeptides, e.g., a 22406 polypeptide having the amino acid sequence shown in SEQ ID NO:2; an amino acid sequence that is substantially identical to the amino acid sequence shown in SEQ ID NO:2; or an amino acid sequence encoded by a nucleic acid molecule having a nucleotide sequence which hybridizes under stringent hybridization conditions to a nucleic acid molecule comprising the nucleotide sequence of SEQ ID NO:1 or SEQ ID NO:3, wherein the nucleic acid encodes a full length 22406 protein or an active fragment thereof.

In a related aspect, the invention further provides nucleic acid constructs which include a 22406 nucleic acid molecule described herein.

In a related aspect, the invention provides 22406 polypeptides or fragments operatively linked to non-22406 polypeptides to form fusion proteins.

In another aspect, the invention features antibodies and antigen-binding fragments thereof, that react with, or more preferably specifically bind 22406 polypeptides.

In another aspect, the invention provides methods of screening for compounds that modulate the expression or activity of the 22406 polypeptides or nucleic acids.

In still another aspect, the invention provides a process for modulating 22406 polypeptide or nucleic acid expression or activity, e.g. using the screened compounds. In certain embodiments, the methods involve treatment of conditions related to aberrant activity or expression of the 22406 polypeptides or nucleic acids, such as conditions involving neurological disorders.

The invention also provides assays for determining the activity of or the presence or absence of 22406 polypeptides or nucleic acid molecules in a biological sample, including for disease diagnosis.

In further aspect the invention provides assays for determining the presence or absence of a genetic alteration in a 22406 polypeptide or nucleic acid molecule, including for disease diagnosis.

BRIEF DESCRIPTION OF THE DRAWINGS

FIGS. 1A–B depicts a cDNA sequence (SEQ ID NO:1) and predicted amino acid sequence (SEQ ID NO:2) of human 22406. The methionine-initiated open reading frame of human 22406 (without the 5' and 3' untranslated regions) extends from nucleotide position 69 to position 1088 of SEQ ID NO:1, not including the terminal codon (coding sequence shown in SEQ ID NO:3).

FIG. 4 shows transmembrane segments predicted by MEMSAT and Prosite matches for the 22406 open reading frame for amino acids corresponding to specific functional sites. For the cAMP-and cGMP-dependent protein kinase phosphorylation site, the actual modified residue is the last amino acid. For the protein kinase C phosphorylation sites, the actual modified residue is the first amino acid. For the casein kinase II phosphorylation sites, the actual modified residue is the first amino acid. For the N-myristoylation site, the actual modified residue is the first amino acid. In addition, Prosite matches the protein of the invention to a serine/threonine dehydratase pyridoxal-phosphate attachment site at about amino acids 47–60.

FIG. 5 shows expression of the 22406 protein in various normal human tissues.

FIG. 6 shows the PSORT prediction of protein localization.

FIGS. 7A–B depicts an alignment of the pyridoxal-phosphate dependent enzyme family member domain (PALP) of human 22406 with a consensus amino acid sequence derived from a hidden Markov model. The upper sequence is the consensus amino acid sequence (SEQ ID NO:4), while the lower amino acid sequence corresponds to amino acids 19 to 315 of SEQ ID NO:2.

FIG. 8 displays the ProDom matches for 22406.

Figure 2:
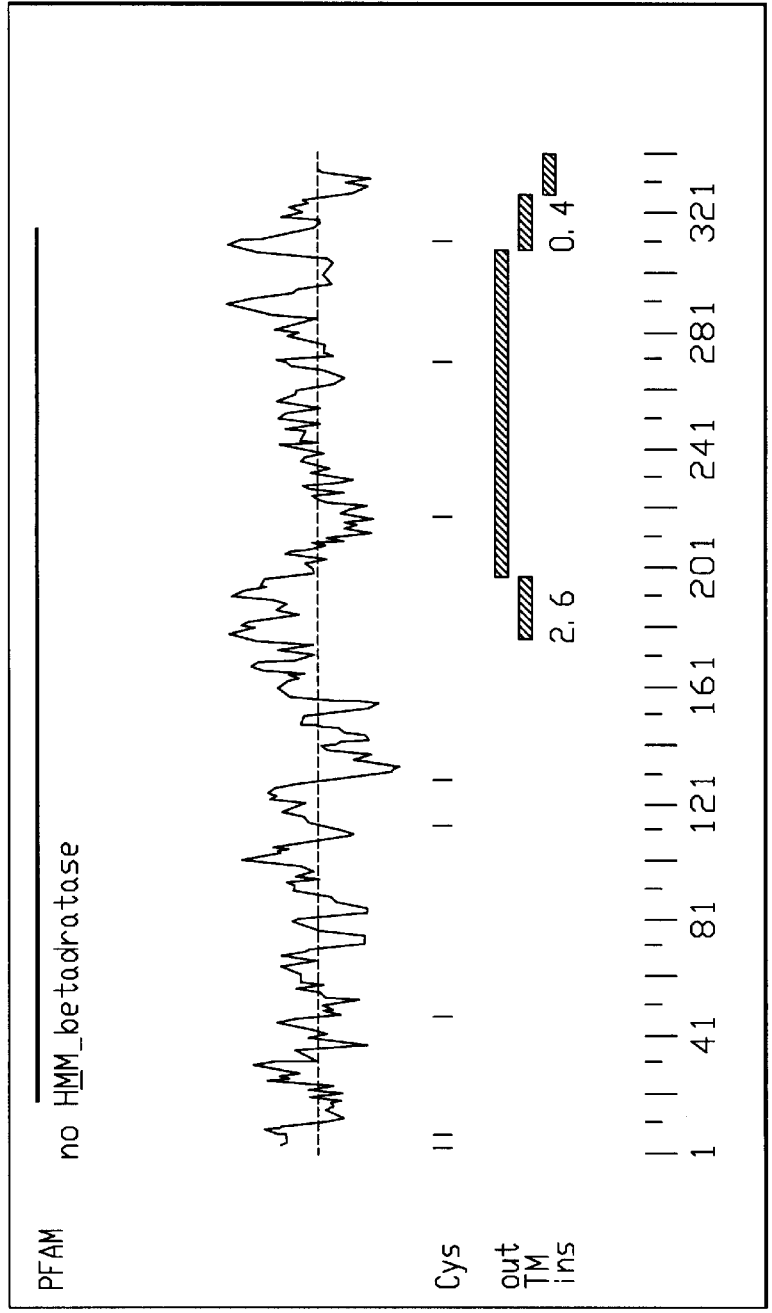
FIG. 2 depicts a hydropathy plot of human 22406. Relative hydrophobic residues are shown above the dashed horizontal line, and relative hydrophilic residues are below the dashed horizontal line. The cysteine residues (cys) and N glycosylation site (Ngly) are indicated by short vertical lines just below the hydropathy trace. The numbers corresponding to the amino acid sequence (shown in SEQ ID NO:2) of human 22406 are indicated. Polypeptides of the invention include fragments which include: all or a part of a hydrophobic sequence (a sequence above the dashed line); or all or part of a hydrophilic fragment (a sequence below the dashed line). Other fragments include a cysteine residue or an N-glycosylation site. Predicted transmembrane domains (TM) are also depicted.
Figure 3:
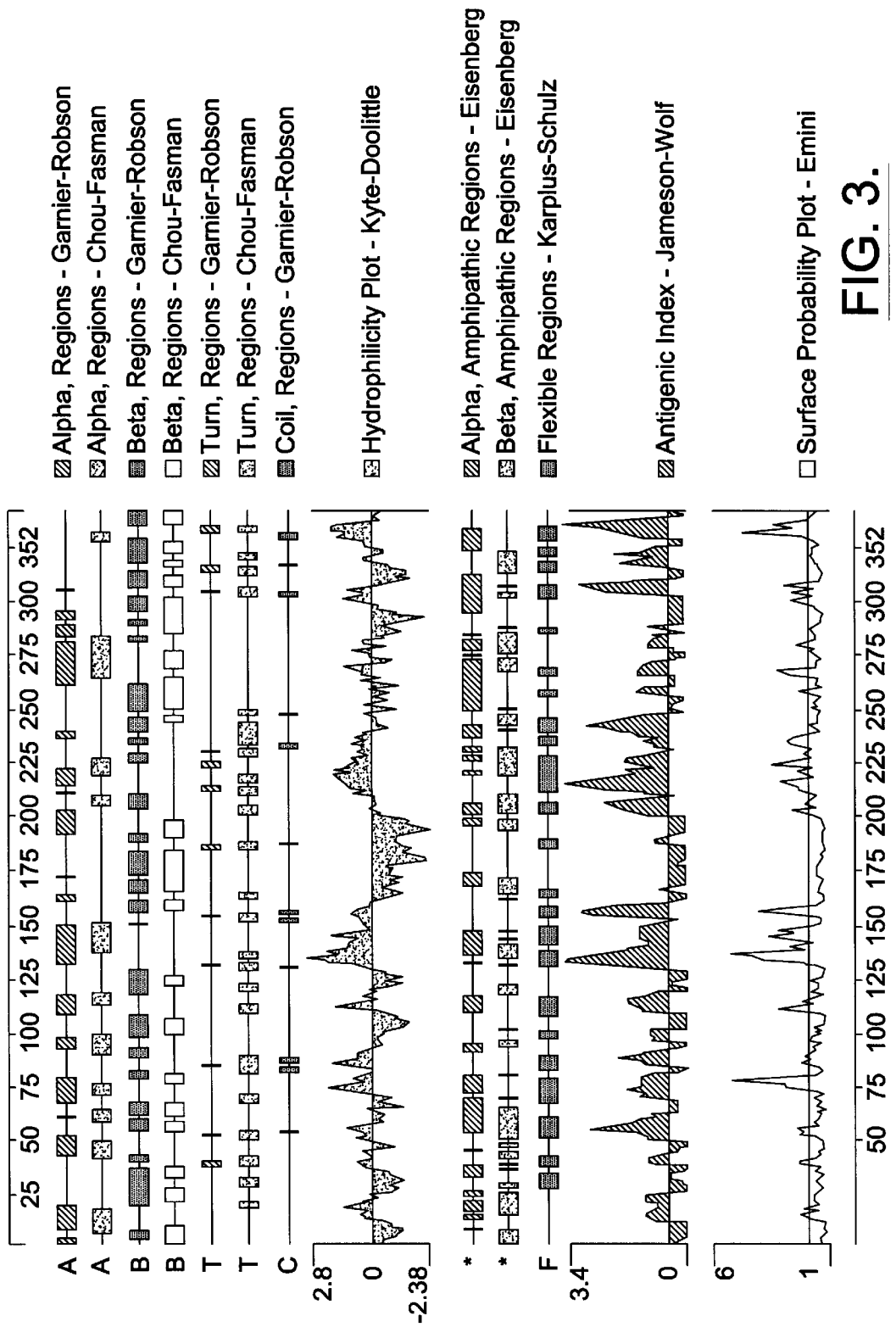
FIG. 3 shows an analysis of the 22406 amino acid sequence: αβturn and coil regions; hydrophilicity; amphipathic regions; flexible regions; antigenic index; and surface probability plot.

Other features and advantages of the invention will be apparent from the following detailed description, and from the claims.

DETAILED DESCRIPTION OF THE INVENTION

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Human 22406

The human 22406 sequence (FIGS. 1A–B; SEQ ID NO:1), which is approximately 1770 nucleotides long including untranslated regions, contains a predicted methionine-initiated coding sequence of about 1020 nucleotides (nucleotides 69–1088 of SEQ ID NO:1; SEQ ID NO:3), not including the terminal codon. The coding sequence encodes a 340 amino acid protein (SEQ ID NO:2). Chromosome mapping localized the gene to human chromosome 17 between D17S849 and D17S796 (0.6–14cM).

Human 22406 contains a predicted pyridoxal-phosphate dependent enzyme family member domain (PALP) (PFAM Accession PF00291) located at about amino acid residues 19–315 of SEQ ID NO:2 (FIG. 7). The annotation "S_T_dehydratase" in the PFAM alignment of FIG. 7 reflects a change in nomenclature of the Pfam identifier for this class of enzyme domain. Human 22406 is also predicted to contain two transmembrane domains which extend from about amino acid residues 176–197 and 308–326 of SEQ ID NO:2 (FIG. 4).

The results of a BLASTX search reveal that the amino acid sequence of 22406 shares about 90% sequence identity and about 96% sequence similarity with a murine serine racemase (Accession No. AF148321). Similar results of a BLASTN search reveal that the nucleotide sequence of 22406 shares about 88% sequence identity with this murine serine racemase (Accession No. AAF08701). This serine racemase is a member of the pyridoxal-phosphate dependent family of enzymes with the Pfam identifier, PALP, (Wolosker et al. (1999) *PNAS* 96:13409–13414).

Members of the pyridoxal-phosphate dependent enzymes frequently have the pyridoxal-phosphate group attached via a lysine residue. The sequence around this residue is sufficiently conserved to allow the derivation of a pattern specific to pyridoxal-phosphate dependent enzymes. This pyridoxal-phosphate attachment site consensus pattern (SEQ ID NO:5) is as follows:

[DESH]-x(4,5)-[STVG]-x-[AS]-[FYI]-K-[DLIFSA]-[RVMF]-[GA]-[LIVMGA]

In this sequence the "x" can represent any amino acid and the brackets indicate that any of the amino acids contained within are allowed at that position. The "K" is the lysine pyridoxal-phosphate attachment site. The 22406 polypeptide contains such a consensus pattern at amino acid residues 47–60 (FIG. 4). The annotation "Dehydratase_Ser_Thr" rather than "PALP" in this figure reflects the fact that the Pfam identifier for this class of enzyme domain has been recently been updated from Dehydratase_Ser_Thr to PALP.

For general information regarding PFAM identifiers, PS prefix and PF prefix domain identification numbers, refer to Sonnhammer et al. (1997) *Protein* 28:405–420.

The 22406 protein contains a significant number of structural characteristics in common with members of the pyridoxal-phosphate dependent enzyme family. The term "family" when referring to the protein and nucleic acid molecules of the invention means two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin as well as other distinct proteins of human origin, or alternatively, can contain homologues of non-human origin, e.g., rat or mouse proteins. Members of a family can also have common functional characteristics.

As used herein, the term "pyridoxal-phosphate dependent enzyme family member" refers to a protein or polypeptide which is capable of metabolism of amino acids. As referred to herein, pyridoxal-phosphate dependent family members preferably include a catalytic domain of about 100–340 amino acid residues in length, preferably about 200–320 amino acid residues in length, or more preferably about 250–310 amino acid residues in length. A pyridoxal-phosphate dependent enzyme family member typically includes at least one of block of homology known as a pyridoxal-phosphate attachment site characterized by the following motif and described above: [DESH]-x(4,5)-[STVG]-x-[AS]-[FYI]-K-[DLIFSA]-[RVMF]-[GA]-[LIVMGA] (SEQ ID NO:5). Specificity of a pyridoxal-phosphate dependent enzyme family member for catalysis of a particular amino acid metabolic reaction is determined by sequence identity to such a particular sub-class of pyridoxal-phosphate dependent enzyme family members.

For example, the 22406 nucleotide and amino acid sequences of the invention contain high sequence identity to the serine racemase class of pyridoxal-phosphate dependent enzymes as described above and found in Wolosker et al. (1999) *PNAS* 96:13409–13414, herein incorporated by reference in its entirety. Based on this sequence similarity, the 22406 molecules of the present invention are predicted to have similar biological activities as pyridoxal-phosphate dependent serine racemase enzyme family members.

Typically, pyridoxal-phosphate dependent enzyme family members play a role in diverse cellular processes. For example, the metabolism of amino acids involves specific reactions catalyzed by various pyridoxal-phosphate dependent enzyme family members. The pyridoxal-phosphate dependent serine racemase enzymes catalyze the formation of D-serine from L-serine. This reaction is important as D-serine is the endogenous ligand for the glycine site of the glutamate N-methyl-D-aspartate (NMDA) receptor (Mothet et al. (2000) *PNAS* 97:4926–4931). In the brain D-serine co-activates post-synaptic NMDA receptors together with glutamate. NMDA receptor function has been shown to be a mediator of behavioral changes associated with a variety of neurological disorders. Thus, the molecules of the present invention may be involved in one or more of: 1) catalyzation of the formation of D-serine from L-serine; 2) the activation of NMDA receptors; 3) learning; 4) memory; 5) convulsion; 6) anxiety; 7) psychotomimetic induced abnormal behavior; 8) cerebellar ataxia; and 9) neurodengeneration.

A 22406 polypeptide can include a "pyridoxal-phosphate dependent enzyme family member domain" or regions homologous with an "pyridoxal-phosphate dependent enzyme family member domain".

As used herein, the term "pyridoxal-phosphate dependent enzyme family member domain" includes an amino acid sequence of about 100–340 amino acid residues in length and having a bit score for the alignment of the sequence to the pyridoxal-phosphate dependent enzyme family member domain (HMM) of at least 8. Preferably, an pyridoxal-phosphate dependent enzyme family member domain includes at least about 200–320 amino acids, more preferably about 250–310 amino acid residues, or about 290–300 amino acids and has a bit score for the alignment of the sequence to the pyridoxal-phosphate dependent enzyme family member domain (HMM) of at least 16 or greater. The pyridoxal-phosphate dependent enzyme family member domain (HMM) has been assigned the PFAM Accession PF00291 (http://pfam.wustl.edu/). An alignment of the pyridoxal-phosphate dependent enzyme family member domain (amino acids 19 to 315 of SEQ ID NO:2) of human 22406 with a consensus amino acid sequence derived from a hidden Markov model is depicted in FIG. 7.

In a preferred embodiment 22406 polypeptide or protein has a "pyridoxal-phosphate dependent enzyme family member domain (PALP)" or a region which includes at least about 200–320, more preferably about 250–310 or 290–300 amino acid residues and has at least about 60%, 70%, 80%, 90%, 95%, 99%, or 100% homology with a "PALP domain," e.g., the pyridoxal-phosphate dependent enzyme family member domain of human 22406 (e.g., amino acid residues 19–315 of SEQ ID NO:2).

To identify the presence of an "pyridoxal-phosphate dependent enzyme family member" domain in a 22406 protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM search). For example, the hmmsf program, which is available as part of the HMMER package of search programs, is a family specific default program for MILPAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

In one embodiment, a 22406 protein includes at least one transmembrane domain. As used herein, the term "transmembrane domain" includes an amino acid sequence of about 15 amino acid residues in length that spans a phospholipid membrane. More preferably, a transmembrane domain includes about at least 18, 20, 22, 24, 25, 30, 35 or 40 amino acid residues and spans a phospholipid membrane. Transmembrane domains are rich in hydrophobic residues, and typically have an α-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, http://pfam.wustl.edu/cgi-bin/getdesc?name=7tm-1, and Zagotta W. N. et al. (1996) *Annual Rev. Neuronsci.* 19:235–63, the contents of which are incorporated herein by reference.

In one embodiment, a 22406 polypeptide or protein has at least one transmembrane domain or a region which includes at least 18, 20, 22, 24, 25, 30, 35 or 40 amino acid residues and has at least about 60%, 70% 80% 90% 95%, 99%, or 100% homology with a "transmembrane domain," e.g., at least one transmembrane domain of human 22406 (e.g., amino acid residues 176–197 and 308–326 of SEQ ID NO:2).

In one embodiment, a 22406 protein includes at least one "non-transmembrane domain." As used herein, "non-transmembrane domains" are domains that reside outside of the membrane. When referring to plasma membranes, non-transmembrane domains include extracellular domains (i.e., outside of the cell) and intracellular domains (i.e., within the cell). When referring to membrane-bound proteins found in intracellular organelles (e.g., mitochondria, endoplasmic reticulum, peroxisomes and microsomes), non-transmembrane domains include those domains of the protein that reside in the cytosol (i.e., the cytoplasm), the lumen of the organelle, or the matrix or the intermembrane space (the latter two relate specifically to mitochondria organelles). The C-terminal amino acid residue of a non-transmembrane domain is adjacent to an N-terminal amino acid residue of a transmembrane domain in a naturally-occurring 22406 protein, or 22406-like protein.

In one embodiment a 22406 polypeptide or protein has at least one "non-transmembrane domain" or a region which includes at least about 1–175 acid residues, and has at least about 60%, 70% 80% 90% 95%, 99% or 100% homology with a "non-transmembrane domain", e.g., a non-transmembrane domain of human 22406 (e.g., residues 1–175, 198–307, and 327–340 of SEQ ID NO:2). Preferably, a non-transmembrane domain is capable of catalytic activity (e.g., catalyzing a serine racemazation reaction).

As the 22406 polypeptides of the invention may modulate 22406-mediated activities, they may be useful as of for developing novel diagnostic and therapeutic agents for 22406-mediated or related disorders, as described below.

As used herein, a "22406 activity", "biological activity of 22406" or "functional activity of 22406", refers to an activity exerted by a 22406 protein, polypeptide or nucleic acid molecule on e.g., a 22406-responsive cell or on a 22406 substrate, e.g., an amino acid substrate, as determined in vivo or in vitro. In one embodiment, a 22406 activity is a direct activity, such as an association with a 22406 target molecule. A "target molecule" or "binding partner" is a molecule with which a 22406 protein binds or interacts in nature, e.g., an amino acid such as L-serine or D-serine. A 22406 activity can also be an indirect activity, e.g., a cellular signaling activity mediated by interaction of the D-serine product of 22406 catalysis with a D-serine "receptor", "target molecule" or "binding partner". A D-serine "receptor", "target molecule" or "binding partner" is herein defined as a molecule with which D-serine binds or interacts in nature, and these terms are herein used interchangeably. For example, the 22406 proteins of the present invention can have one or more of the following activities: 1) catalyzation of the formation of D-serine from L-serine; 2) activation of the NMDA receptor; 3) mediation of learning; 4) mediation of memory; 5) mediation of convulsion; 6) mediation of anxiety; 7) mediation of psychotomimetic induced abnormal behavior; 8) mediation of cerebellar ataxia; 9) mediation of neurodengeneration and 10) the ability to modulate, competitively or non-competitively, any of 1–10. "Modulate" is herein defined as increasing or decreasing an activity or process by any mechanism, including but not limited to, inhibition or antagonism by competitive or non-competitive binding.

Accordingly, 22406 protein may mediate various disorders, particularly brain disorders, including but not limited to, behavioral changes associated with learning, memory, convulsion, anxiety, psychotomimetic induced abnormal behavior, cerebellar ataxia, and neurodengeneration. Inhibitors of 22406 protein can be expected to quell anxiety and epilepsy and to prevent damage from stroke and certain neurodegenerative conditions including Alzheimer's disease. On the other hand, stimulating 22406 protein might improve schizophrenia symptoms, which are partly caused by depressed NMDA receptor function.

Figure 9A:
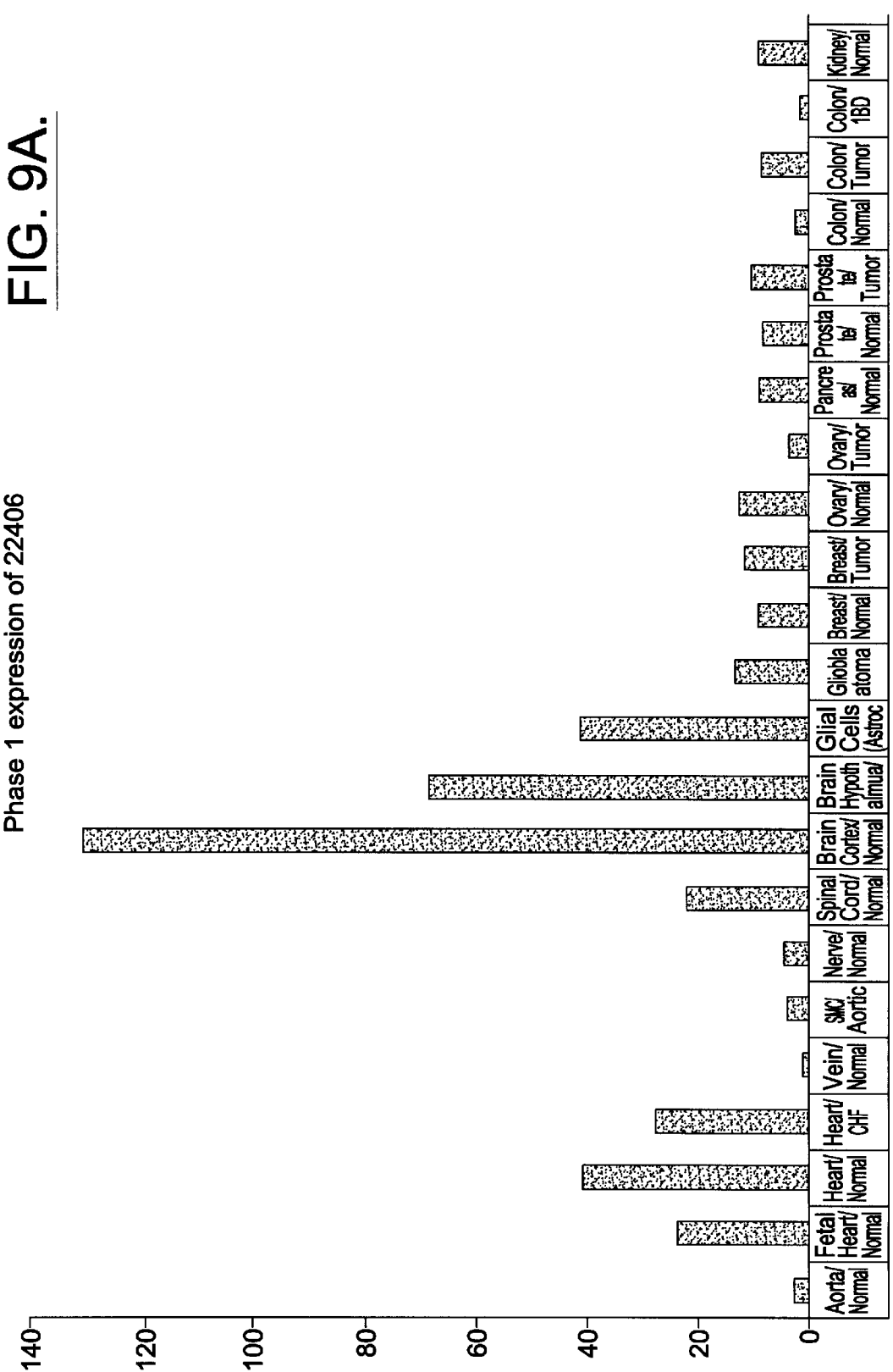
FIGS. 9A–B displays the expression levels of 22406 in various tissues determined by quantitative PCR. The highest level of expression is observed in brain cortex. The tissue types are as follows from left to right: Aorta/Normal, Fetal Heart/Normal, Heart/Normal, Heart/CHF, Vein/Normal, SMC/Aortic, Nerve/Normal, Spinal Cord/Normal, Brain Cord/Normal, Brain Cortex/Normal, Brain Hypothalmus/Normal, Glial Cells (Astrocytes), Glioblastoma, Breast/Normal, Breast/Tumor, Ovary/Normal, Ovary/Tumor, Pancreas/Normal, Prostate/Normal, Prostate/Tumor, Colon/Normal, Colon/Tumor, Colon/IBD, Kidney/Normal, Liver/Normal, Liver/Fibrosis, Fetal Liver/Normal, Lung/Normal, Lung/COPD, Spleen/Normal, Tonsil/Normal, Lymph Node/Normal, Thymus/Normal, Epithelial Cells (Prostate), Endothelial Cells (Aortic), Skeletal Muscle/Normal, Fibroblasts (Dermal), Skin/Normal, Adipose/Normal, Osteoblasts (Primary), Osteoblasts (Undiff), Osteoblasts (Diff), Osteoclasts, NTC.
Figure 9B:
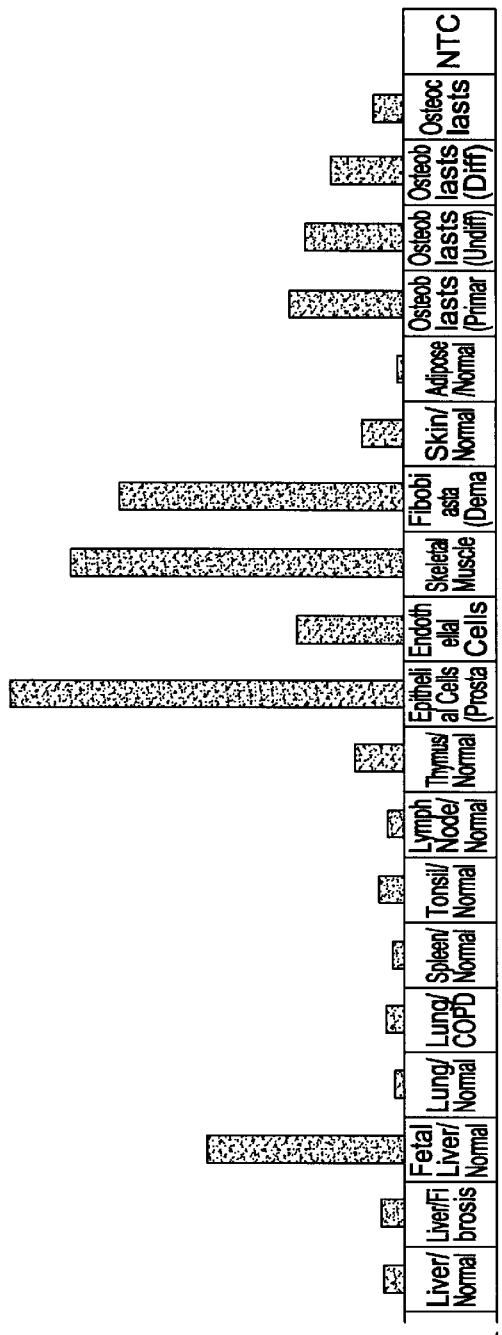

In addition, 22406 protein can be expected to be involved in various disorders of the tissues in which it is expressed. FIGS. 5 and 9 show expression of the 22406 protein in various normal human tissues with highest expression in brain, heart, liver, skeletal muscle, lymph node, prostate, dermal fibroblast, testes, and thymus. Significant expression is also found in various other tissues. In addition to the tissues shown in the Figures, expression has also been observed in adrenal gland, bone, endothelial cells, total fetal tissue, hypothalamus, keratinocytes, natural killer cells, osteoblasts, pituitary, skin, spinal cord, T-cells, colon to liver metastases and lymphoma.

Expression was also observed in two separate lung tumor cDNA libraries while libraries of normal lung and bronchial epithelia sequenced to equal depths yielded no sequences for the 22406 protein. Additionally, PCR analysis on panels containing normal and tumor lung cDNAs showed that the gene may be expressed at higher levels in lung tumor samples. Expression was also observed in colonic tumor cDNA libraries.

Thus, 22406 can be also be expected to be involved in disorders including heart disorders, liver disorders, lung disorders, prostrate disorders, colon disorders, skeletal muscle disorders, dermal fibroblast disorders, lymph node disorders, and blood vessel disorders.

Disorders involving the brain include, but are not limited to, disorders involving neurons, and disorders involving glia, such as astrocytes, oligodendrocytes, ependymal cells, and microglia; cerebral edema, raised intracranial pressure and herniation, and hydrocephalus; malformations and developmental diseases, such as neural tube defects, forebrain anomalies, posterior fossa anomalies, and syringomyelia and hydromyelia; perinatal brain injury; cerebrovascular diseases, such as those related to hypoxia, ischemia, and infarction, including hypotension, hypoperfusion, and low-flow states—global cerebral ischemia and focal cerebral ischemia—infarction from obstruction of local blood supply, intracranial hemorrhage, including intracerebral (intraparenchymal) hemorrhage, subarachnoid hemorrhage and ruptured berry aneurysms, and vascular malformations, hypertensive cerebrovascular disease, including lacunar infarcts, slit hemorrhages, and hypertensive encephalopathy; infections, such as acute meningitis, including acute pyogenic (bacterial) meningitis and acute aseptic (viral) meningitis, acute focal suppurative infections, including brain abscess, subdural empyema, and extradural abscess, chronic bacterial meningoencephalitis, including tuberculosis and mycobacterioses, neurosyphilis, and neuroborreliosis (Lyme disease), viral meningoencephalitis, including arthropod-borne (Arbo) viral encephalitis, Herpes simplex virus Type 1, Herpes simplex virus Type 2, Varicalla-zoster virus (Herpes zoster), cytomegalovirus, poliomyelitis, rabies, and human immunodeficiency virus 1, including HIV-1 meningoencephalitis (subacute encephalitis), vacuolar myelopathy, AIDS-associated myopathy, peripheral neuropathy, and AIDS in children, progressive multifocal leukoencephalopathy, subacute sclerosing panencephalitis, fungal meningoencephalitis, other infectious diseases of the nervous system; transmissible spongiform encephalopathies (prion diseases); demyelinating diseases, including multiple sclerosis, multiple sclerosis variants, acute disseminated encephalomyelitis and acute necrotizing hemorrhagic encephalomyelitis, and other diseases with demyelination; degenerative diseases, such as degenerative diseases affecting the cerebral cortex, including Alzheimer disease and Pick disease, degenerative diseases of basal ganglia and brain stem, including Parkinsonism, idiopathic Parkinson disease (paralysis agitans), progressive supranuclear palsy, corticobasal degeneration, multiple system atrophy, including striatonigral degeneration, Shy-Drager syndrome, and olivopontocerebellar atrophy, and Huntington disease; spinocerebellar degenerations, including spinocerebellar ataxias, including Friedreich ataxia, and ataxia-telanglectasia, degenerative diseases affecting motor neurons, including amyotrophic lateral sclerosis (motor neuron disease), bulbospinal atrophy (Kennedy syndrome), and spinal muscular atrophy; inborn errors of metabolism, such as leukodystrophies, including Krabbe disease, metachromatic leukodystrophy, adrenoleukodystrophy, Pelizaeus-Merzbacher disease, and Canavan disease, mitochondrial encephalomyopathies, including Leigh disease and other mitochondrial encephalomyopathies; toxic and acquired metabolic diseases, including vitamin deficiencies such as thiamine (vitamin $B_1$) deficiency and vitamin $B_{12}$ deficiency, neurologic sequelae of metabolic disturbances, including hypoglycemia, hyperglycemia, and hepatic encephatopathy, toxic disorders, including carbon monoxide, methanol, ethanol, and radiation, including combined methotrexate and radiation-induced injury; tumors, such as gliomas, including astrocytoma, including fibrillary (diffuse) astrocytoma and glioblastoma multiforme, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma), and neurocutaneous syndromes (phakomatoses), including neurofibromotosis, including Type 1 neurofibromatosis (NF1) and TYPE 2 neurofibromatosis (NF2), tuberous sclerosis, and Von Hippel-Lindau disease.

Disorders involving the heart, include but are not limited to, heart failure, including but not limited to, cardiac hypertrophy, left-sided heart failure, and right-sided heart failure; ischemic heart disease, including but not limited to angina pectoris, myocardial infarction, chronic ischemic heart disease, and sudden cardiac death; hypertensive heart disease, including but not limited to, systemic (left-sided) hypertensive heart disease and pulmonary (right-sided) hypertensive heart disease; valvular heart disease, including but not limited to, valvular degeneration caused by calcification, such as calcific aortic stenosis, calcification of a congenitally bicuspid aortic valve, and mitral annular calcification, and myxomatous degeneration of the mitral valve (mitral valve prolapse), rheumatic fever and rheumatic heart disease, infective endocarditis, and noninfected vegetations, such as nonbacterial thrombotic endocarditis and endocarditis of systemic lupus erythematosus (Libman-Sacks disease), carcinoid heart disease, and complications of artificial valves; myocardial disease, including but not limited to dilated cardiomyopathy, hypertrophic cardiomyopathy, restrictive cardiomyopathy, and myocarditis; pericardial disease, including but not limited to, pericardial effusion and hemopericardium and pericarditis, including acute pericarditis and healed pericarditis, and rheumatoid heart disease; neoplastic heart disease, including but not limited to, primary cardiac tumors, such as myxoma, lipoma, papillary fibroelastoma, rhabdomyoma, and sarcoma, and cardiac effects of noncardiac neoplasms; congenital heart disease, including but not limited to, left-to-right shunts—late cyanosis, such as atrial septal defect, ventricular septal defect, patent ductus arteriosus, and atrioventricular septal defect, right-to-left shunts—early cyanosis, such as tetralogy of fallot, transposition of great arteries, truncus arteriosus, tricuspid atresia, and total anomalous pulmonary venous connection, obstructive congenital anomalies, such as coarctation of aorta, pulmonary stenosis and atresia, and aortic stenosis and atresia, and disorders involving cardiac transplantation.

Disorders involving blood vessels include, but are not limited to, responses of vascular cell walls to injury, such as endothelial dysfunction and endothelial activation and intimal thickening; vascular diseases including, but not limited to, congenital anomalies, such as arteriovenous fistula, atherosclerosis, and hypertensive vascular disease, such as hypertension; inflammatory disease—the vasculitides, such as giant cell (temporal) arteritis, Takayasu arteritis, polyarteritis nodosa (classic), Kawasaki syndrome (mucocutaneous lymph node syndrome), microscopic polyanglitis (microscopic polyarteritis, hypersensitivity or leukocytoclastic anglitis), Wegener granulomatosis, thromboanglitis obliterans (Buerger disease), vasculitis associated with other disorders, and infectious arteritis; Raynaud disease; aneurysms and dissection, such as abdominal aortic aneurysms, syphilitic (luetic) aneurysms, and aortic dissection (dissecting hematoma); disorders of veins and lymphatics, such as varicose veins, thrombophlebitis and phlebothrombosis, obstruction of superior vena cava (superior vena cava syndrome), obstruction of inferior vena cava (inferior vena cava syndrome), and lymphangitis and lymphedema; tumors, including benign tumors and tumor-like conditions, such as hemangioma, lymphangioma, glomus tumor (glomangioma), vascular ectasias, and bacillary angiomatosis, and intermediate-grade (borderline low-grade malignant) tumors, such as Kaposi sarcoma and hemangloendothelioma, and malignant tumors, such as angiosarcoma and hemangiopericytoma; and pathology of therapeutic interventions in vascular disease, such as balloon angioplasty and related techniques and vascular replacement, such as coronary artery bypass graft surgery.

Disorders involving the liver include, but are not limited to, hepatic injury; jaundice and cholestasis, such as bilirubin and bile formation; hepatic failure and cirrhosis, such as cirrhosis, portal hypertension, including ascites, portosystemic shunts, and splenomegaly; infectious disorders, such as viral hepatitis, including hepatitis A–E infection and infection by other hepatitis viruses, clinicopathologic syndromes, such as the carrier state, asymptomatic infection, acute viral hepatitis, chronic viral hepatitis, and fulminant hepatitis; autoimmune hepatitis; drug- and toxin-induced liver disease, such as alcoholic liver disease; inborn errors of metabolism and pediatric liver disease, such as hemochromatosis, Wilson disease, $\alpha_1$-antitrypsin deficiency, and neonatal hepatitis; intrahepatic biliary tract disease, such as secondary biliary cirrhosis, primary bliary cirrhosis, primary sclerosing cholangitis, and anomalies of the biliary tree; circulatory disorders, such as impaired blood flow into the liver, including hepatic artery compromise and portal vein obstruction and thrombosis, impaired blood flow through the liver, including passive congestion and centrilobular necrosis and peliosis hepatis, hepatic vein outflow obstruction, including hepatic vein thrombosis (Budd-Chiari syndrome) and veno-occlusive disease; hepatic disease associated with pregnancy, such as preeclampsia and eclampsia, acute fatty liver of pregnancy, and intrehepatic cholestasis of pregnancy; hepatic complications of organ or bone marrow transplantation, such as drug toxicity after bone marrow transplantation, graft-versus-host disease and liver rejection, and nonimmunologic damage to liver allografts; tumors and tumorous conditions, such as nodular hyperplasias, adenomas, and malignant tumors, including primary carcinoma of the liver and metastatic tumors.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the lung, prostate, and colon. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

Disorders involving the colon include, but are not limited to, congenital anomalies, such as atresia and stenosis, Meckel diverticulum, congenital aganglionic megacolon-Hirschsprung disease; enterocolitis, such as diarrhea and dysentery, infectious enterocolitis, including viral gastroenteritis, bacterial enterocolitis, necrotizing enterocolitis, antibiotic-associated colitis (pseudomembranous colitis), and collagenous and lymphocytic colitis, miscellaneous intestinal inflammatory disorders, including parasites and protozoa, acquired immunodeficiency syndrome, transplantation, drug-induced intestinal injury, radiation enterocolitis, neutropenic colitis (typhlitis), and diversion colitis; idiopathic inflammatory bowel disease, such as Crohn disease and ulcerative colitis; tumors of the colon, such as non-neoplastic polyps, adenomas, familial syndromes, colorectal carcinogenesis, colorectal carcinoma, and carcinoid tumors.

Disorders involving the prostate include, but are not limited to, inflammations, benign enlargement, for example, nodular hyperplasia (benign prostatic hypertrophy or hyperplasia), and tumors such as carcinoma.

Disorders involving precursor T-cell neoplasms include precursor T lymphoblastic leukemia/lymphoma. Disorders involving peripheral T-cell and natural killer cell neoplasms include T-cell chronic lymphocytic leukemia, large granular lymphocytic leukemia, mycosis fungoides and Sezary syndrome, peripheral T-cell lymphoma, unspecified, angio-immunoblastic T-cell lymphoma, angiocentric lymphoma (NK/T-cell lymphoma[4a]), intestinal T-cell lymphoma, adult T-cell leukemia/lymphoma, and anaplastic large cell lymphoma.

Disorders involving the skeletal muscle include tumors such as rhabdomyosarcoma.

The 22406 protein, fragments thereof, and derivatives and other variants of the sequence in SEQ ID NO:2 are collectively referred to as "polypeptides or proteins of the invention" or "22406 polypeptides or proteins". Nucleic acid molecules encoding such polypeptides or proteins are collectively referred to as "nucleic acids of the invention" or "22406 nucleic acids." 22406 molecules refer to 22406 nucleic acids, polypeptides, and antibodies.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA.

The term "isolated or purified nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

As used herein, the term "hybridizes under stringent conditions" describes conditions for hybridization and washing. Stringent conditions are known to those skilled in the art and can be found in *Current Protocols in Molecular Biology* John Wiley & Sons, N.Y. (1989), 6.3.1–6.3.6. Aqueous and nonaqueous methods are described in that reference and either can be used. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45° C., followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

As used herein, the terms "gene" and "recombinant gene" refer to nucleic acid molecules which include an open reading frame encoding a 22406 protein, preferably a mammalian 22406 protein, and can further include non-coding regulatory sequences, and introns.

An "isolated" or "purified" polypeptide or protein is substantially free of cellular material or other contaminating proteins from the cell or tissue source from which the protein is derived, or substantially free from chemical precursors or other chemicals when chemically synthesized. In one embodiment, the language "substantially free" means preparation of 22406protein having less than about 30%, 20%, 10% and more preferably 5% (by dry weight), of non-22406 protein (also referred to herein as a "contaminating protein"), or of chemical precursors or non-22406 chemicals. When the 22406 protein or biologically active portion thereof is recombinantly produced, it is also preferably substantially free of culture medium, i.e., culture medium represents less than about 20%, more preferably less than about 10%, and most preferably less than about 5% of the volume of the protein preparation. The invention includes isolated or purified preparations of at least 0.01, 0.1, 1.0, and 10 milligrams in dry weight.

A "non-essential" amino acid residue is a residue that can be altered from the wild-type sequence of 22406 (e.g., the sequence of SEQ ID NO:1 or SEQ ID NO:3) without abolishing or more preferably, without substantially altering a biological activity, whereas an "essential" amino acid residue results in such a change. For example, amino acid residues that are conserved among the polypeptides of the present invention, e.g., those present in the pyridoxal-phosphate attachment site, are predicted to be partioularly unamenable to alteration.

A "conservative amino acid substitution" is one in which the amino-acid residue is replaced withsan amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a 22406 protein is preferably replaced with another amino acid residue from the same side chain family. Alternatively, in another embodiment, mutations can be introduced randomly along all or part of a 22406 coding sequence, such as by saturation mutagenesis, and the resultant mutants can be screened for 22406 biological activity to identify mutants that retain activity. Following mutagenesis of SEQ ID NO:1 or SEQ ID NO:3, the encoded protein can be, expressed recombinantly and the activity of the protein can be determined.

As used herein, a "biologically active portion" of a 22406 protein includes a fragment of a 22406 protein which participates in an interaction between a 22406 molecule and a non-22406 molecule. Biologically active portions of a 22406 protein include peptides comprising amino acid sequences sufficiently homologous to or derived from the amino acid sequence of the 22406 protein, e.g., the amino acid sequence shown in SEQ ID NO:2, which include less amino acids than the full length 22406 proteins, and exhibit at least one activity of a 22406 protein. Typically, biologically active portions comprise a domain or motif with at least one activity of the 22406 protein, e.g., pyridoxal-phosphate dependent enzyme family member activity. A biologically active portion of a 22406 protein can be a polypeptide which is, for example, 10, 25, 50, 100, 200 or more amino acids in length. Biologically active portions of a 22406 protein can be used as targets for developing agents which modulate a 22406 mediated activity, e.g., pyridoxal-phosphate dependent enzyme family member activity.

Calculations of homology or sequence identity between sequences (the terms are used interchangeably herein) are performed as follows.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence (e.g., when aligning a second sequence to the 22406 amino acid sequence of SEQ ID NO:2 having 340 amino acid residues, at least 102, preferably at least 136, more preferably at least 170, even more preferably at least 204, and even more preferably at least 238, 272, 306 or 340 amino acid residues are aligned. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a finction of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 22406 nucleic acid molecules of the invention. BLAST protein searches can be performed with the XBLAST program, score=50, wordlength=3 to obtain amino acid sequences homologous to 22406 protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

"Subject", as used herein, can refer to a mammal, e.g., a human, or to an experimental or animal or disease model. The subject can also be a non-human animal, e.g., a horse, cow, goat, or other domestic animal.

A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

Various aspects of the invention are described in further detail below.

Isolated Nucleic Acid Molecules

In one aspect, the invention provides, an isolated or purified, nucleic acid molecule that encodes a 22406 polypeptide described herein, e.g., a full length 22406 protein or a fragment thereof, e.g., a biologically active portion of 22406 protein. Also included is a nucleic acid fragment suitable for use as a hybridization probe, which can be used, e.g., to a identify nucleic acid molecule encoding a polypeptide of the invention, 22406 mRNA, and fragments suitable for use as primers, e.g., PCR primers for the amplification or mutation of nucleic acid molecules.

In one embodiment, an isolated nucleic acid molecule of the invention includes the nucleotide sequence shown in SEQ ID NO:1, or a portion of this nucleotide sequence. In one embodiment, the nucleic acid molecule includes sequences encoding the human 22406 protein (i.e., "the coding region", from nucleotides 69–1088 of SEQ ID NO:1, not including the terminal codon), as well as 5' untranslated sequences (nucleotides 1–68 of SEQ ID NO:1). Alternatively, the nucleic acid molecule can include only the coding region of SEQ ID NO:1 (e.g., nucleotides 69–1088 of SEQ ID NO:1, corresponding to SEQ ID NO:3) and, e.g., no flanking sequences which normally accompany the subject sequence. In another embodiment, the nucleic acid molecule encodes a sequence corresponding to the mature protein of SEQ ID NO:2.

In another embodiment, an isolated nucleic acid molecule of the invention includes a nucleic acid molecule which is a complement of the nucleotide sequence shown in SEQ ID NO:1 or SEQ ID NO:3, or a portion of any of these nucleotide sequences. In other embodiments, the nucleic acid molecule of the invention is sufficiently complementary to the nucleotide sequence shown in SEQ ID NO:1 or SEQ ID NO:3 such that it can hybridize to the nucleotide sequence shown in SEQ ID NO:1 or SEQ ID NO:3, thereby forming a stable duplex.

In one embodiment, an isolated nucleic acid molecule of the present invention includes a nucleotide sequence which is at least about 95%, 96%, 97%, 98%, 99%, or more homologous to the nucleotide sequence shown in SEQ ID NO:1 or SEQ ID NO:3. In the case of an isolated nucleic acid molecule which is longer than or equivalent in length to the reference sequence, e.g., SEQ ID NO:1 or SEQ ID NO:3, the comparison is made with the full length of the reference sequence. Where the isolated nucleic acid molecule is shorter than the reference sequence, e.g., shorter than SEQ ID NO:1 or SEQ ID NO:3, the comparison is made to a segment of the reference sequence of the same length (excluding any loop required by the homology calculation).

22406 Nucleic Acid Fragments

A nucleic acid molecule of the invention can include only a portion of the nucleic acid sequence of SEQ ID NO:1 or SEQ ID NO:3. For example, such a nucleic acid molecule can include a fragment which can be used as a probe or primer or a fragment encoding a portion of a 22406 protein, e.g., an immunogenic or biologically active portion of a 22406 protein. A fragment can comprise: nucleotides 19–315 of SEQ ID NO:1, which encodes an pyridoxal-phosphate dependent enzyme family member domain of human 22406. Alternatively, a fragment can comprise: nucleotides 47–60 of SEQ ID NO:1, which encodes an pyridoxal-phosphate attachment site of human 22406. The nucleotide sequence determined from the cloning of the 22406 gene allows for the generation of probes and primers designed for use in identifyng and/or cloning other 22406 family members, or fragments thereof, as well as 22406 homologues, or fragments thereof, from other species.

In another embodiment, a nucleic acid includes a nucleotide sequence that includes part, or all, of the coding region and extends into either (or both) the 5' or 3' noncoding region. Other embodiments include a fragment which includes a nucleotide sequence encoding an amino acid fragment described herein. Nucleic acid fragments can encode a specific domain or site described herein or fragments thereof, particularly fragments thereof which are at least 150 amino acids in length. Fragments also include nucleic acid sequences corresponding to specific amino acid sequences described above or fragments thereof. Nucleic acid fragments should not to be construed as encompassing those fragments that may have been disclosed prior to the invention.

A nucleic acid fragment can include a sequence corresponding to a domain, region, or functional site described herein. A nucleic acid fragment can also include one or more domain, region, or functional site described herein. Thus, for example, the nucleic acid fragment can include an pyridoxal-phosphate dependent enzyme family member domain. In a preferred embodiment the fragment is at least, 50, 100, 200, 300, 400, 500, 600, 700, or 885 base pairs in length.

22406 probes and primers are provided. Typically a probe/primer is an isolated or purified oligonucleotide. The oligonucleotide typically includes a region of nucleotide sequence that hybridizes under stringent conditions to at least about 15, 20, 25, 30, 35, 40, 45, 50, 55, 60, 65, or 75 consecutive nucleotides of a sense or antisense sequence of SEQ ID NO:1 or SEQ ID NO:3, or of a naturally occurring allelic variant or mutant of SEQ ID NO:1 or SEQ ID NO:3.

In one embodiment the nucleic acid is a probe which is at least 5, 10, 20 or 30, and less than 200, more preferably less than 100, or less than 50, base pairs in length. It should be identical, or differ by 1, or less than in 5 or 10 bases, from a sequence disclosed herein. If alignment is needed for this comparison the sequences should be aligned for maximum homology. "Looped" out sequences from deletions or insertions, or mismatches, are considered differences.

A probe or primer can be derived from the sense or anti-sense strand of a nucleic acid which encodes a 22406 pyridoxal-phosphate dependent enzyme family member domain (e.g., about amino acid residues 19–315 of SEQ ID NO:2).

In another embodiment a set of primers is provided, e.g., primers suitable for use in a PCR, which can be used to amplify a selected region of a 22406 sequence, e.g., a region described herein. The primers should be at least 5, 10, 20, 30, or 50 base pairs in length and less than 100, or less than 200, base pairs in length. The primers should be identical, or differs by one base from a sequence disclosed herein or ftom a naturally occurring variant; e.g., primers suitable for amplifying all or a portion of any of the following regions are provided: a 22406 pyridoxal-phosphate dependent enzyme family member domain (e.g., about amino acid residues 19–315 of SEQ ID NO:2).

A nucleic acid fragment can encode an epitope bearing region of a polypeptide described herein.

A nucleic acid fragment encoding a "biologically active portion of a 22406 polypeptide" can be prepared by isolating a portion of the nucleotide sequence of SEQ ID NO:1 or SEQ ID NO:3, which encodes a polypeptide having a 22406 biological activity (e.g., the biological activities of the 22406 proteins as described herein), expressing the encoded portion of the 22406 protein (e.g., by recombinant expression in vitro) and assessing the activity of the encoded portion of the 22406 protein. For example, a nucleic acid fragment encoding a biologically active portion of 22406 includes a pyridoxal-phosphate dependent enzyme family member domain (e.g., about amino acid residues 19–315 of SEQ ID NO:2). A nucleic acid fragment encoding a biologically active portion of a 22406 polypeptide, may comprise a nucleotide sequence which is greater than 300–885 or more nucleotides in length.

In preferred embodiments, nucleic acids include a nucleotide sequence which is about 100, 200, 300, 400, 500, 600, 700, 800, 900, 1000, 1100, 1200, 1300, 1400, 1500, 1600, 1700 nucleotides in length and hybridizes under stringent hybridization conditions to a nucleic acid molecule of SEQ ID NO:1 or SEQ ID NO:3. A fragment of a nucleotide sequence of the present invention comprises a nucleotide sequence consisting of nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1600, 1600–1700, 1700–1770 of SEQ ID NO:1.

22406 Nucleic Acid Variants

The invention further encompasses nucleic acid molecules that differ from the nucleotide sequence shown in SEQ ID NO:1 or SEQ ID NO:3. Such differences can be due to degeneracy of the genetic code and result in a nucleic acid that encodes the same 22406 proteins as those encoded by the nucleotide sequence disclosed herein. In another embodiment, an isolated nucleic acid molecule of the invention has a nucleotide sequence encoding a protein having an amino acid sequence which differs, by at least 1, but less than 5, 10, 20, 50, or 100 amino acid residues that is shown in SEQ ID NO:2. If alignment is needed for this comparison the sequences should be aligned for maximum homology. "Looped" out sequences from deletions or insertions, or mismatches, are considered differences.

Nucleic acids of the invention can be chosen for having codons, which are preferred, or non preferred, for a particular expression system; e.g., the nucleic acid can be one in which at least one codon, at preferably at least 10%, or 20% of the codons has been altered such that the sequence is optimized for expression in *E. coli*, yeast, human, insect, or CHO cells.

Nucleic acid variants can be naturally occurring, such as allelic variants (same locus), homologs (different locus), and orthologs (different organism) or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product).

In a preferred embodiment, the nucleic acid differs from that of SEQ ID NO:1 or SEQ ID NO:3, e.g., as follows: by at least one but less than 10, 20, 30, or 40 nucleotides; or at least one but less than 1%, 5%, 10% or 20% of the in the subject nucleic acid. If necessary for this analysis the sequences should be aligned for maximum homology. "Looped" out sequences from deletions or insertions, or mismatches, are considered differences.

Orthologs, homologs, and allelic variants can be identified using methods known in the art. These variants comprise a nucleotide sequence encoding a polypeptide that is at least about 95%, 96%, 97%, 98%, 99% or more identical to the amino acid sequence shown in SEQ ID NO:2 or a fragment of this sequence. Such nucleic acid molecules can readily be obtained as being able to hybridize under stringent conditions, to the nucleotide sequence shown in SEQ ID NO:3 or a fragment of this sequence. Nucleic acid molecules corresponding to orthologs, homologs, and allelic variants of the 22406 cDNAs of the invention can further be isolated by mapping to the same chromosome or locus as the 22406 gene. Preferred variants include those that are correlated with pyridoxal-phosphate dependent racemase activity.

Allelic variants of 22406, e.g., human 22406, include both functional and non-functional proteins. Functional allelic variants are naturally occurring amino acid sequence variants of the 22406 protein within a population that maintain the ability to form D-serine from L-serine. Functional allelic variants will typically contain only conservative substitution of one or more amino acids of SEQ ID NO:2, or substitution, deletion or insertion of non-critical residues in non-critical regions of the protein. Non-functional allelic variants are naturally-occurring amino acid sequence variants of the 22406, e.g., human 22406, protein within a population that do not have the ability to form D-serine from L-serine. Non-functional allelic variants will typically contain a non-conservative substitution, a deletion, or insertion, or premature truncation of the amino acid sequence of SEQ ID NO:2, or a substitution, insertion, or deletion in critical residues or critical regions of the protein.

Moreover, nucleic acid molecules encoding other 22406 family members and, thus, which have a nucleotide sequence which differs from the 22406 sequences of SEQ ID NO:1 or SEQ ID NO:3 are intended to be within the scope of the invention.

Antisense Nucleic Acid Molecules, Ribozymes and Modified 22406 Nucleic Acid Molecules In another aspect, the invention features, an isolated nucleic acid molecule which is antisense to 22406. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire 22406 coding strand, or to only a portion thereof (e.g., the coding region of human 22406 corresponding to SEQ ID NO:3). In another embodiment, the antisense nucleic acid molecule is antisense to a "noncoding region" of the coding strand of a nucleotide sequence encoding 22406 (e.g., the 5' and 3' untranslated regions).

An antisense nucleic acid can be designed such that it is complementary to the entire coding region of 22406 mRNA, but more preferably is an oligonucleotide which is antisense to only a portion of the coding or noncoding region of 22406 mRNA. For example, the antisense oligonucleotide can be complementary to the region surrounding the translation start site of 22406 mRNA, e.g., between the −10 and +10 regions of the target gene nucleotide sequence of interest. An antisense oligonucleotide can be, for example, about 7, 10, 15, 20, 25, 30, 35, 40, 45, 50, 55, 60, 65, 70, 75, 80, or more nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject (e.g., by direct injection at a tissue site), or generated in situ such that they hybridize with or bind to cellular mRNA and/or genomic DNA encoding a 22406 protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBSLett.* 215:327–330).

In still another embodiment, an antisense nucleic acid of the invention is a ribozyme. A ribozyme having specificity for a 22406-encoding nucleic acid can include one or more sequences complementary to the nucleotide sequence of a 22406 cDNA disclosed herein (i.e., SEQ ID NO:1, or SEQ ID NO:3), and a sequence having known catalytic sequence responsible for mRNA cleavage (see U.S. Pat. No. 5,093, 246 or Haselhoff and Gerlach (1988) *Nature* 334:585–591). For example, a derivative of a Tetrahymena L-19 IVS RNA can be constructed in which the nucleotide sequence of the active site is complementary to the nucleotide sequence to be cleaved in a 22406-encoding mRNA. See, e.g., Cech et al. U.S. Pat. No. 4,987,071; and Cech et al. U.S. Pat. No. 5,116,742. Alternatively, 22406 mRNA can be used to select a catalytic RNA having a specific ribonuclease activity from a pool of RNA molecules. See, e.g., Bartel, D. and Szostak, J. W. (1993) *Science* 261:1411–1418.

22406 gene expression can be inhibited by targeting nucleotide sequences complementary to the regulatory region of the 22406 (e.g., the 22406 promoter and/or enhancers) to form triple helical structures that prevent transcription of the 22406 gene in target cells. See generally, Helene (1991) *Anticancer Drug Des.* 6(6):569–84; Helene et al. (1992) *Ann. N.Y. Acad. Sci.* 660:27–36; and Maher (1992) *Bioassays* 14(12):807–15. The potential sequences that can be targeted for triple helix formation can be increased by creating a so-called "switchback" nucleic acid molecule. Switchback molecules are synthesized in an alternating 5'–3', 3'–5' manner, such that they base pair with first one strand of a duplex and then the other, eliminating the necessity for a sizeable stretch of either purines or pyrimidines to be present on one strand of a duplex.

The invention also provides detectably labeled oligonucleotide primer and probe molecules. Typically, such labels are chemiluminescent, fluorescent, radioactive, or colorimetric.

A 22406 nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorganic & Medicinal Chemistry* 4 (1): 5–23). As used herein, the terms "peptide nucleic acid" or "PNA" refers to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996) supra; Perry-O'Keefe et al. *Proc. Natl. Acad. Sci.* 93:14670–675.

PNAs of 22406 nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of 22406 nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup (1996) supra)); or as probes or primers for DNA sequencing or hybridization (Hyrup et al. (1996) supra; Perry-O'Keefe supra).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553–6556; Lemaitre et al. (1987) *Proc. Natl. Acad. Sci. USA* 84:648–652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958–976) or intercalating agents. (See, e.g., Zon (1988) *Pharm. Res.* 5:539–549). To this end, the oligonucleotide may be conjugated to another molecule, (e.g., a peptide, hybridization triggered cross-linking agent, transport agent, or hybridization-triggered cleavage agent).

The invention also includes molecular beacon oligonucleotide primer and probe molecules having at least one region which is complementary to a 22406 nucleic acid of the invention, two complementary regions one having a fluorophore and one a quencher such that the molecular beacon is useful for quantitating the presence of the 22406 nucleic acid of the invention in a sample. Molecular beacon nucleic acids are described, for example, in Lizardi et al. U.S. Pat. No. 5,854,033; Nazarenko et al. U.S. Pat. No. 5,866,336, and Livak et al. U.S. Pat. No. 5,876,930.

Isolated 22406 Polypeptides

In another aspect, the invention features, an isolated 22406 protein, or fragment, e.g., a biologically active portion, for use as immunogens or antigens to raise or test (or more generally to bind) anti-22406 antibodies. 22406 protein can be isolated from cells or tissue sources using standard protein purification techniques. 22406 protein or fragments thereof can be produced by recombinant DNA techniques or synthesized chemically.

Polypeptides of the invention include those which arise as a result of the existence of multiple genes, alternative transcription events, alternative RNA splicing events, and alternative translational and postranslational events. The polypeptide can be expressed in systems, e.g., cultured cells, which result in substantially the same postranslational modifications present when expressed the polypeptide is expressed in a native cell, or in systems which result in the alteration or omission of postranslational modifications, e.g., glycosylation or cleavage, present when expressed in a native cell.

In a preferred embodiment, a 22406 polypeptide has one or more of the following characteristics:

(i) it has the ability to form D-serine from L-serine;

(ii) it has a molecular weight, e.g., a deduced molecular weight, amino acid composition or other physical characteristic of the polypeptide of SEQ ID NO:2;

(iii) it has an overall sequence identity of at least 95%, 96%, 97%, 98%, or 99%, with a polypeptide of SEQ ID NO:2;

(iv) it has an pyridoxal-phosphate dependent enzyme family member domain which preferably has an overall sequence identity of about 70%, 80%, 90% or 95% with amino acid residues 19–315 of SEQ ID NO:2;

(v) it has a pyridoxal-phosphate attachment site conserved sequence as described herein; and (vi) it has at least 70%, preferably 80%, and most preferably 95% of the cysteines found amino acid sequence of the native protein.

In a preferred embodiment the 22406 protein, or fragment thereof, differs from one but by less than 15, 10 or 5 amino acid residues. In another it differs from the corresponding sequence in SEQ ID NO:2 by at least one residue but less than 20%, 15%, 10% or 5% of the residues in it differ from the corresponding sequence in SEQ ID NO:2. (If this comparison requires alignment the sequences should be aligned for maximum homology. "Looped" out sequences from deletions or insertions, or mismatches, are considered differences.) The differences are, preferably, differences or changes at a non-essential residue or a conservative substitution. In a preferred embodiment the differences are not in the pyridoxal-phosphate dependent enzyme family member domain. In another preferred embodiment one or more differences are in non-active site residues, e.g. outside of the pyridoxal-phosphate dependent enzyme family member domain.

Other embodiments include a protein that contain one or more changes in amino acid sequence, e.g., a change in an amino acid residue which is not essential for activity. Such 22406 proteins differ in amino acid sequence from SEQ ID NO:2, yet retain biological activity.

In one embodiment, a biologically active portion of a 22406 protein includes an pyridoxal-phosphate dependent enzyme family member domain. In another embodiment, a biologically active portion of a 22406 protein includes a pyridoxal-phosphate attachment site domain. Moreover, other biologically active portions, in which other regions of the protein are deleted, can be prepared by recombinant techniques and evaluated for one or more of the functional activities of a native 22406 protein.

In a preferred embodiment, the 22406 protein has an amino acid sequence shown in SEQ ID NO:2. In other embodiments, the 22406 protein is substantially identical to SEQ ID NO:2. In yet another embodiment, the 22406 protein is substantially identical to SEQ ID NO:2 and retains the functional activity of the protein of SEQ ID NO:2, as described in detail above. Accordingly, in another embodiment, the 22406 protein is a protein which includes an amino acid sequence at least about 95%, 96%, 97%, 98%, 99%, or more identical to SEQ ID NO:2.

22406 Chimeric or Fusion Proteins

In another aspect, the invention provides 22406 chimeric or fusion proteins. As used herein, a 22406 "chimeric protein" or "fusion protein" includes a 22406 polypeptide linked to a non-22406 polypeptide. A "non-22406 polypeptide" refers to a polypeptide having an amino acid sequence corresponding to a protein which is not substantially homologous to the 22406 protein, e.g., a protein which is different from the 22406 protein and which is derived from the same or a different organism. The 22406 polypeptide of the fusion protein can correspond to all or a portion e.g., a fragment described herein of a 22406 amino acid sequence. In a preferred embodiment, a 22406 fusion protein includes at least one (or two) biologically active portion of a 22406 protein. The non-22406 polypeptide can be fused to the N-terminus or C-terminus of the 22406 polypeptide.

The fusion protein can include a moiety which has a high affinity for a ligand. For example, the fusion protein can be a GST-22406 fusion protein in which the 22406 sequences are fused to the C-terminus of the GST sequences. Such fusion proteins can facilitate the purification of recombinant 22406. Alternatively, the fusion protein can be a 22406 protein containing a heterologous signal sequence at its N-terminus. In certain host cells (e.g., mammalian host cells), expression and/or secretion of 22406 can be increased through use of a heterologous signal sequence.

Fusion proteins can include all or a part of a serum protein; e.g., an IgG constant region, or human serum albumin.

The 22406 fusion proteins of the invention can be incorporated into pharmaceutical compositions and administered to a subject in vivo. The 22406 fusion proteins can be used to affect the bioavailability of a 22406 substrate. 22406 fusion proteins may be useful therapeutically for the treatment of disorders caused by, for example, (i) aberrant modification or mutation of a gene encoding a 22406 protein; (ii) misregulation of the 22406 gene; and (iii) aberrant post-translational modification of a 22406 protein.

Moreover, the 22406-fusion proteins of the invention can be used as immunogens to produce anti-22406 antibodies in a subject, to purify 22406 ligands and in screening assays to identify molecules which inhibit the interaction of 22406 with a 22406 substrate.

Expression vectors are commercially available that already encode a fusion moiety (e.g., a GST polypeptide). A 22406-encoding nucleic acid can be cloned into such an expression vector such that the fusion moiety is linked in-frame to the 22406 protein.

Variants of 22406 Proteins

In another aspect, the invention also features a variant of a 22406 polypeptide, e.g., which functions as an agonist (mimetics or with increased activity) or as an antagonist (with decreased activity as a competitive inhibitor). Variants of the 22406 proteins can be generated by mutagenesis, e.g., discrete point mutation, the insertion or deletion of sequences or the truncation of a 22406 protein. An agonist of the 22406 proteins can possess increased activity, or retain substantially the same, or a subset, of the biological activities of the naturally occurring form of a 22406 protein. An antagonist of a 22406 protein can inhibit one or more of the activities of the naturally occurring form of the 22406 protein by, for example, competitively modulating a 22406-mediated activity of a 22406 protein. Thus, specific biological effects can be elicited by treatment with a variant of limited function. Preferably, treatment of a subject with a variant having a subset of the biological activities of the naturally occurring form of the protein has fewer side effects in a subject relative to treatment with the naturally occurring form of the 22406 protein.

Variants of a 22406 protein can be identified by screening combinatorial libraries of mutants, e.g., truncation mutants, of a 22406 protein for agonist or antagonist actiyity.

Libraries of fragments e.g., N terminal, C terminal, or internal fragments, of a 22406 protein coding sequence can be used to generate a variegated population of fragments for screening and subsequent selection of variants of a 22406 protein.

Variants in which a cysteine residues is added or deleted or in which a residue which is glycosylated is added or deleted are particularly preferred.

Methods for screening gene products of combinatorial libraries made by point mutations or truncation, and for screening cDNA libraries for gene products having a selected property. Recursive ensemble mutagenesis (REM), a new technique which enhances the frequency of functional mutants in the libraries, can be used in combination with the screening assays to identify 22406 variants (Arkin and Yourvan (1992) *Proc. Natl. Acad. Sci. USA* 89:7811–7815; Delgrave et al. (1993) *Protein Engineering* 6(3):327–331).

Cell based assays can be exploited to analyze a variegated 22406 library. For example, a library of expression vectors can be transfected into a cell line, e.g., a cell line, which ordinarily responds to 22406 in a substrate-dependent manner. The transfected cells are then contacted with D-serine and the effect of the expression of the mutant on signaling by the D-serine 22406 substrate can be detected, e.g., by measuring serine racemase activity. Plasmid DNA can then be recovered from the cells which score for inhibition, or alternatively, potentiation of signaling by the 22406 substrate, and the individual clones further characterized.

In another aspect, the invention features a method of making a 22406 polypeptide, e.g., a peptide having a non-wild type activity, e.g., increased or decreased activity relative to a naturally occurring 22406 polypeptide. The method includes: altering the sequence of a 22406 polypeptide, e.g., altering the sequence, e.g., by substitution or deletion of one or more residues of a non-conserved region, a domain or residue disclosed herein, and testing the altered polypeptide for the desired activity.

In another aspect, the invention features a method of making a fragment or analog of a 22406 polypeptide a biological activity of a naturally occurring 22406 polypeptide. The method includes: altering the sequence, e.g., by substitution or deletion of one or more residues, of a 22406 polypeptide, e.g., altering the sequence of a non-conserved region, or a domain or residue described herein, and testing the altered polypeptide for the desired activity.

Anti-22406 Antibodies

In another aspect, the invention provides an anti-22406 antibody. The term "antibody" as used herein refers to an immunoglobulin molecule or immunologically active portion thereof, i.e., an antigen-binding portion. Examples of immunologically active portions of immunoglobulin molecules include F(ab) and F(ab')$_2$ fragments which can be generated by treating the antibody with an enzyme such as pepsin.

The antibody can be a polyclonal, monoclonal, recombinant, e.g., a chimeric or humanized, fully human, non-human, e.g., murine, or single chain antibody. In a preferred embodiment it has effector function and can fix complement. The antibody can be coupled to a toxin or imaging agent.

A full-length 22406 protein or, antigenic peptide fragment of 22406 can be used as an immunogen or can be used to identify anti-22406 antibodies made with other immunogens, e.g., cells, membrane preparations, and the like. The antigenic peptide of 22406 should include at least 8 amino acid residues of the amino acid sequence shown in SEQ ID NO:2 and encompasses an epitope of 22406. Preferably, the antigenic peptide includes at least 10 amino acid residues, more preferably at least 15 amino acid residues, even more preferably at least 20 amino acid residues, and most preferably at least 30 amino acid residues.

Fragments of 22406 which include, e.g., residues 130–150 of SEQ ID NO:2 of SEQ ID NO:5 can be used to make, e.g., used as immunogens, or used to characterize the specificity of an antibody or antibodies against what are believed to be hydrophilic regions of the 22406 protein. Similarly, a fragment of 22406 which includes, e.g., residues 175–200 of SEQ ID NO:2 can be used to make an antibody against what is believed to be a hydrophobic region of the 22406 protein; a fragment of 22406 which includes residues 45–62 of SEQ ID NO:2 can be used to make an antibody against the pyridoxal-phosphate dependent enzyme family member region of the 22406 protein.

Antibodies reactive with, or specific for, any of these regions, or other regions or domains described herein are provided.

In a preferred embodiment the antibody fails to bind an Fc receptor, e.g. it is a type which does not support Fc receptor binding or has been modified, e.g., by deletion or other mutation, such that is does not have a functional Fc receptor binding region.

Preferred epitopes encompassed by the antigenic peptide are regions of 22406 are located on the surface of the protein, e.g., hydrophilic regions, as well as regions with high antigenicity. For example, an Emini surface probability analysis of the human 22406 protein sequence can be used to indicate the regions that have a particularly high probability of being localized to the surface of the 22406 protein and are thus likely to constitute surface residues useful for targeting antibody production.

In a preferred embodiment the antibody binds an epitope on any domain or region on 22406 proteins described herein.

Chimeric, humanized, but most preferably, completely human antibodies are desirable for applications which include repeated administration, e.g., therapeutic treatment (and some diagnostic applications) of human patients.

The anti-22406 antibody can be a single chain antibody. A single-chain antibody (scFV) may be engineered (see, for example, Colcher et al. (Jun. 30, 1999) *Ann. NY Acad. Sci.*880:263–80; and Reiter (1996 February) *Clin. Cancer Res.*2(2):245–52). The single chain antibody can be dimerized or multimerized to generate multivalent antibodies having specificities for different epitopes of the same target 22406 protein.

An anti-22406 antibody (e.g., monoclonal antibody) can be used to isolate 22406 by standard techniques, such as affinity chromatography or immunoprecipitation. Moreover, an anti-22406 antibody can be used to detect 22406 protein (e.g., in a cellular lysate or cell supernatant) in order to evaluate the abundance and pattern of expression of the protein. Anti-22406 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance (i.e., antibody labeling). Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^3$H.

Recombinant Expression Vectors, Host Cells and Genetically Engineered Cells

In another aspect, the invention includes, vectors, preferably expression vectors, containing a nucleic acid encoding a polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a 22406 nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., 22406 proteins, mutant forms of 22406 proteins, fusion proteins, and the like).

The recombinant expression vectors of the invention can be designed for expression of 22406 proteins in prokaryotic or eukaryotic cells. For example, polypeptides of the invention can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharnacia Biotech Inc; Smith et al. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be used in 22406 activity assays, (e.g., direct assays or competitive assays described in detail below), or to generate antibodies specific for 22406 proteins. In a preferred embodiment, a fusion protein expressed in a retroviral expression vector of the present invention can be used to infect bone marrow cells which are subsequently transplanted into irradiated recipients. The pathology of the subject, recipient is then examined after sufficient time has passed (e.g., six (6) weeks).

To maximize recombinant protein expression in *E. coli* is to express the protein in host bacteria with an impaired capacity to proteolytically cleave the recombinant protein (Gottesman, *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al. (1992) *Nucleic Acids Res.* 20:2111–2118). Such alteration of nucleic acid sequences of the invention can be carried out by standard DNA synthesis techniques.

The 22406 expression vector can be a yeast expression vector, a vector for expression in insect cells, e.g., a baculovirus expression vector or a vector suitable for expression in mammalian cells.

When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374–379) and the α-fetoprotein promoter (Campes and Tilghman (1989) *Genes Dev.* 3:537–546).

The invention further provides a recombinant expression vector comprising a DNA molecule of the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus. For a discussion of the regulation of gene expression using antisense genes see Weintraub et al. (1986) Antisense RNA as a molecular tool for genetic analysis, *Reviews—Trends in Genetics*, Vol. 1(1).

Another aspect the invention provides a.host cell which includes a nucleic acid molecule described herein, e.g., a 22406 nucleic acid molecule within a recombinant expression vector or a 22406 nucleic acid molecule containing sequences which allow it to homologously recombine into a specific site of the host cell's genome. The terms "host cell" and "recombinant host cell" are used interchangeably herein. Such terms refer not only to the particular subject cell but rather also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a 22406 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell of the invention can be used to produce (i.e., express) a 22406 protein. Accordingly, the invention further provides methods for producing a 22406 protein using the host cells of the invention. In one embodiment, the method includes culturing the host cell of the invention (into which a recombinant expression vector encoding a 22406 protein has been introduced) in a suitable medium such that a 22406 protein is produced. In another embodiment, the method further includes isolating a 22406 protein from the medium or the host cell.

In another aspect, the invention features, a cell or purified preparation of cells which include a 22406 transgene, or which otherwise misexpress 22406. The cell preparation can consist of human or non-human cells, e.g., rodent cells, e.g., mouse or rat cells, rabbit cells, or pig cells. In preferred embodiments, the cell or cells include a 22406 transgene, e.g., a heterologous form of a 22406, e.g., a gene derived from humans (in the case of a non-human cell). The 22406 transgene can be misexpressed, e.g., overexpressed or underexpressed. In other preferred embodiments, the cell or cells include a gene which misexpress an endogenous 22406, e.g., a gene the expression of which is disrupted, e.g., a knockout. Such cells can serve as a model for studying disorders which are related to mutated or misexpressed 22406 alleles or for use in drug screening.

In another aspect, the invention features, a human cell, e.g., a brain cell, transformed with nucleic acid which encodes a subject 22406 polypeptide.

Also provided are cells or a purified preparation thereof, e.g., human cells, in which an endogenous 22406 is under the control of a regulatory sequence that does not normally control the expression of the endogenous 22406 gene. The expression characteristics of an endogenous gene within a cell, e.g., a cell line or microorganism, can be modified by inserting a heterologous DNA regulatory element into the genome of the cell such that the inserted regulatory element is operably linked to the endogenous 22406 gene. For example, an endogenous 22406 gene, e.g., a gene which is "transcriptionally silent," e.g., not normally expressed, or expressed only at very low levels, may be activated by inserting a regulatory element which is capable of promoting the expression of a normally expressed gene product in that cell. Techniques such as targeted homologous recombinations, can be used to insert the heterologous DNA as described in, e.g., Chappe, U.S. Pat. No. 5,272,071; WO 91/06667, published on May 16, 1991.

Transgenic Animals

The invention provides non-human transgenic animals. Such animals are useful for studying the function and/or activity of a 22406 protein and for identifying and/or evaluating modulators of 22406 activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA or a rearrangement, e.g., a deletion of endogenous chromosomal DNA, which preferably is integrated into or occurs in the genome of the cells of a transgenic animal. A transgene can direct the expression of an encoded gene product in one or more cell types or tissues of the transgenic animal, other transgenes, e.g., a knockout, reduce expression. Thus, a transgenic animal can be one in which an endogenous 22406 gene has been altered by, e.g., by homologous recombination between the endogenous gene and an exogenous DNA molecule introduced into a cell of the animal, e.g., an embryonic cell of the animal, prior to development of the animal.

Intronic sequences and polyadenylation signals can also be included in the transgene to increase the efficiency of expression of the transgene. A tissue-specific regulatory sequence(s) can be operably linked to a transgene of the invention to direct expression of a 22406 protein to particular cells. A transgenic founder animal can be identified based upon the presence of a 22406 transgene in its genome and/or expression of 22406 mRNA in tissues or cells of the animals. A transgenic founder animal can then be used to breed additional animals carrying the transgene. Moreover, transgenic animals arrying a transgene encoding a 22406 protein can further be bred to other transgenic animals carrying other transgenes.

22406 proteins or polypeptides can be expressed in transgenic animals or plants, e.g., a nucleic acid encoding the protein or polypeptide can be introduced into the genome of an animal. In preferred embodiments the nucleic acid is placed under the control of a tissue specific promoter, e.g., a milk or egg specific promoter, and recovered from the milk or eggs produced by the animal. Suitable animals are mice, pigs, cows, goats, and sheep.

The invention also includes a population of cells from a transgenic animal, as discussed herein.

Uses

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic).

The isolated nucleic acid molecules of the invention can be used, for example, to express a 22406 protein (e.g., via a recombinant expression vector in a host cell in gene therapy applications), to detect a 22406 mRNA (e.g., in a biological sample) or a genetic alteration in a 22406 gene, and to modulate 22406 activity, as described further below. The 22406 proteins can be used to treat disorders characterized by insufficient or excessive production of a 22406 substrate or production of 22406 inhibitors. In addition, the 22406 proteins can be used to screen for naturally occurring 22406 substrates, to screen for drugs or compounds which modulate 22406 activity, as well as to treat disorders characterized by insufficient or excessive production of 22406 protein or production of 22406 protein forms which have decreased, aberrant or unwanted activity compared to 22406 wild-type protein. Such disorders include those of the brain, particularly those disorders associated with convulsion, anxiety, and neurodengeneration. Moreover, the anti-22406 antibodies of the invention can be used to detect and isolate 22406 proteins, regulate the bioavailability of 22406 proteins, and modulate 22406 activity.

A method of evaluating a compound for the ability to interact with, e.g., bind, a subject 22406 polypeptide is provided. The method includes: contacting the compound with the subject 22406 polypeptide; and evaluating ability of the compound to interact with, e.g., to bind or form a complex with the subject 22406 polypeptide. This method can be performed in vitro, e.g., in a cell free system, or in vivo, e.g., in a two-hybrid interaction trap assay. This method can be used to identify naturally occurring molecules which interact with subject 22406 polypeptide. It can also be used to find natural or synthetic inhibitors of subject 22406 polypeptide. Screening methods are discussed in more detail below.

Screening Assays

The invention provides methods (also referred to herein as "screening assays") for identifying modulators, i.e., candidate or test compounds or agents (e.g., proteins, peptides, peptidomimetics, peptoids, small molecules or other drugs) which bind to 22406 proteins, have a stimulatory or inhibitory effect on, for example, 22406 expression or 22406 activity, or have a stimulatory or inhibitory effect on, for example, the expression or activity of a 22406 substrate. Compounds thus identified can be used to modulate the activity of target gene products (e.g., 22406 genes) in a therapeutic protocol, to elaborate the biological function of the target gene product, or to identify compounds that disrupt normal target gene interactions.

In one embodiment, the invention provides assays for screening candidate or test compounds which are substrates of a 22406 protein or polypeptide or a biologically active portion thereof. In another embodiment, the invention provides assays for screening candidate or test compounds which bind to or modulate the activity of a 22406 protein or polypeptide or a biologically active portion thereof.

The test compounds of the present invention can be obtained using any of the numerous approaches in combinatorial library methods known in the art, including: biological libraries; peptoid libraries [libraries of molecules having the functionalities of peptides, but with a novel, non-peptide backbone which are resistant to enzymatic degradation but which nevertheless remain bioactive] (see, e.g., Zuckermann et al. (1994) *J. Med. Chem.* 37:2678–85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412–421), or on beads (Lam (1991) *Nature* 354:82–84), chips (Fodor (1993) *Nature* 364:555–556), bacteria or spores (Ladner, U.S. Pat. No. 5,223,409), plasmids (Cull et al. (1992) *Proc. Natl. Acad. Sci. USA* 89:1865–1869) or on phage (Scott and Smith (1990) *Science* 249:386–390); (Devlin (1990) *Science* 249:404–406); (Cwirla et al. (1990) *Proc. Natl. Acad. Sci.* 87:6378–6382); (Felici (1991) *J. Mol. Biol.* 222:301–310); (Ladner supra.).

In one embodiment, an assay is a cell-based assay in which a cell which expresses a 22406 protein or biologically active portion thereof is contacted with a test compound, and the ability of the test compound to modulate 22406 activity is determined. Determnining the ability of the test compound to modulate 22406 activity can be accomplished by monitoring, for example, serine racemase activity. The cell, for example, can be of mammalian origin, e.g., human. Cell homogenates, or fractions, preferably membrane containing fractions, can also be tested.

The ability of the test compound to modulate 22406 binding to a compound, e.g., a 22406 substrate, or to bind to 22406 can also be evaluated. This can be accomplished, for example, by coupling the compound, e.g., the substrate, with a radioisotope or enzymatic label such that binding of the compound, e.g., the substrate, to 22406 can be determined by detecting the labeled compound, e.g., substrate, in a complex. Alternatively, 22406 could be coupled with a radioisotope or enzymatic label to monitor the ability of a test compound to modulate 22406 binding to a 22406 substrate in a complex. For example, compounds (e.g., 22406 substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a 22406 substrate) to interact with 22406 with or without the labeling of any of the interactants can be evaluated. For example, a microphysiometer can be used to detect the interaction of a compound with 22406 without the labeling of either the compound or the 22406. McConnell et al. (1992) *Science* 257:1906–1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and 22406.

In yet another embodiment, a cell-free assay is provided in which a 22406 protein or biologically active portion thereof is contacted with a test compound and the ability of the test compound to bind to the 22406 protein or biologically active portion thereof is evaluated. Preferred biologically active portions of the 22406 proteins to be used in assays of the present invention include fragments which participate in interactions with non-22406 molecules,.e.g., fragments with high surface probability scores.

Soluble and/or membrane-bound forms of isolated proteins (e.g., 22406 proteins or biologically active portions thereof) can be used in the cell-free assays of the invention. When membrane-bound forms of the protein are used, it may be desirable to utilize a solubilizing agent. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl-N,N-dimethyl-3-ammonio-1-propane sulfonate.

Cell-free assays involve preparing a reaction mixture of the target gene protein and the test compound under conditions and for a time sufficient to allow the two components to interact and bind, thus forming a complex that can be removed and/or detected.

In one embodiment, assays are performed where the ability of an agent to block pyridoxal-phosphate dependent senne racemase activity within a cell is evaluated.

The interaction between two molecules can also be detected, e.g., using fluorescence energy transfer (FET) (see, for example, Lakowicz et al. U.S. Pat. No. 5,631,169; Stavrianopoulos, et al. U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determining the ability of the 22406 protein to bind to a target molecule can be accomplished using real-time Biomolecular Interaction Analysis (BIA) (see, e.g., Sjolander and Urbaniczky (1991) *Anal. Chem.* 63:2338–2345 and Szabo et al. (1995) *Curr. Opin. Strict. Biol.* 5:699–705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In one embodiment, the target gene product or the test substance is anchored onto a solid phase. The target gene product/test compound complexes anchored on the solid phase can be detected at the end of the reaction. Preferably, the target gene product can be anchored onto a solid surface, and the test compound, (which is not anchored), can be labeled, either directly or indirectly, with detectable labels discussed herein.

It may be desirable to immobilize either 22406, an anti-22406 antibody or its target molecule to facilitate separation of complexed from uncomplexed forms of one or both of the proteins, as well as to accommodate automation of the assay. Binding of a test compound to a 22406 protein, or interaction of a 22406 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase/22406 fusion proteins or glutathione-S-transferase/target fusion proteins can be adsorbed onto glutathione sepharose beads (Sigma Chemical, St. Louis, Mo.) or glutathione derivatized microtiter plates, which are then combined with the test compound or the test compound and either the non-adsorbed target protein or 22406 protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of 22406 binding or activity determined using standard techniques.

Other techniques for immobilizing either a 22406 protein or a target molecule on matrices include using conjugation of biotin and streptavidin. Biotinylated 22406 protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In one embodiment, this assay is performed utilizing antibodies reactive with 22406 protein or target molecules but which do not interfere with binding of the 22406 protein to its target molecule. Such antibodies can be derivatized to the wells of the plate, and unbound target or 22406 protein trapped in the wells by antibody conjugation. Methods for detecting such complexes, in addition to those described above for the GST-immobilized complexes, include immunodetection of complexes using antibodies reactive with the 22406 protein or target molecule, as well as enzyme-linked assays which rely on detecting an enzymatic activity associated with the 22406 protein or target molecule.

Alternatively, cell free assays can be conducted in a liquid phase. In such an assay, the reaction products are separated from unreacted components, by any of a number of standard techniques, including but not limited to: differential centrifugation (see, for example, Rivas and Minton (1993 August) *Trends Biochem Sci* 18(8):284–7); chromatography (gel filtration chromatography, ion-exchange chromatography); electrophoresis (see, e.g., Ausubel et al. eds. *Current Protocols in Molecular Biology* 1999, J. Wiley: New York.); and immunoprecipitation (see, for example, Ausubel et al. eds. *Current Protocols in Molecular Biology* 1999, J. Wiley: New York). Such resins and chromatographic techniques are known to one skilled in the art (see, e.g., Heegaard (1998 Winter) *J. Mol. Recognit.*11(1–6): 141–8; Hage and Tweed (Oct. 10, 1997) *J. Chromatogr. B Biomed. Sci. Appl.*699(1–2):499–525). Further, fluorescence energy transfer may also be conveniently utilized, as described herein, to detect binding without further purification of the complex from solution.

In a preferred embodiment, the assay includes contacting the 22406 protein or biologically active portion thereof with a known compound which binds 22406 to form an assay mixture, contacting the assay mixture with a test compound, and determining the ability of the test compound to interact with a 22406 protein, wherein determining the ability of the test compound to interact with a 22406 protein includes determining the ability of the test compound to preferentially bind to 22406 or biologically active portion thereof, or to modulate the activity of a target molecule, as compared to the known compound.

The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product. Such compounds can include, but are not limited to molecules such as antibodies, peptides, and small molecules. The preferred target genes/products for use in this embodiment are the 22406 genes herein identified. In an alternative embodiment, the invention provides methods for determining the ability of the test compound to modulate the activity of a 22406 protein through modulation of the activity of a downstream effector of a 22406 target molecule. For example, the activity of the effector molecule on an appropriate target can be determined, or the binding of the effector to an appropriate target can be determined, as previously described.

To identify compounds that interfere with the interaction between the target gene product and its cellular or extracellular binding partner(s), e.g., a substrate, a reaction mixture containing the target gene product and the binding partner is prepared, under conditions and for a time sufficient, to allow the two products to form complex. In order to test an inhibitory agent, the reaction mixture is provided in the presence and absence of the test compound. The test compound can be initially included in the reaction mixture, or can be added at a time subsequent to the addition of the target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

These assays can be conducted in a heterogeneous or homogeneous format. Heterogeneous assays involve anchoring either the target gene product or the binding partner onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the target gene product or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

In order to conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. For example, a preformed complex of the target gene product and the interactive cellular or extracellular binding partner product is prepared in that either the target gene products or their binding partners are labeled, but the signal generated by the label is quenched due to complex formation (see, e.g., U.S. Pat. No. 4,109,496 that utilizes this approach for immunoassays). The addition of a test substance that competes with and displaces one of the species from the preformed complex will result in the generation of a signal above background. In this way, test substances that disrupt target gene product-binding partner interaction can be identified.

In yet another aspect, the 22406 proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with 22406 ("22406-binding proteins" or "22406-bp") and are involved in 22406 activity. Such 22406-bps can be activators or inhibitors of signals by the 22406 proteins or 22406 targets as, for example, downstream elements of a 22406-mediated signaling pathway.

The two-hybrid system is based on the modular nature of most transcription factors, which consist of separable DNA-binding and activation domains. Briefly, the assay utilizes two different DNA constructs. In one construct, the gene that codes for a 22406 protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. (Alternatively the: 22406 protein can be the fused to the activator domain.) If the "bait" and the "prey" proteins are able to interact, in vivo, forming a 22406-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the 22406 protein.

In another embodiment, modulators of 22406 expression are identified. For example, a cell or cell free mixture is contacted with a candidate compound and the expression of 22406 mRNA or protein evaluated relative to the level of expression of 22406 mRNA or protein in the absence of the candidate compound. When expression of 22406 mRNA or protein is greater in the presence of the candidate compound than in its absence, the candidate compound is identified as a stimulator of 22406 mRNA or protein expression. Alternatively, when expression of 22406 mRNA or protein is less (statistically significantly less) in the presence of the candidate compound than in its absence, the candidate compound is identified as an inhibitor of 22406 mRNA or protein expression. The level of 22406 mRNA or protein expression can be determined by methods described herein for detecting 22406 mRNA or protein.

In another aspect, the invention pertains to a combination of two or more of the assays described herein. For example, a modulating agent can be identified using a cell-based or a cell free assay, and the ability of the agent to modulate the activity of a 22406 protein can be confirmed in vivo, e.g., in an animal.

This invention further pertains to novel agents identified by the above-described screening assays. Accordingly, it is within the scope of this invention to further use an agent identified as described herein (e.g., a 22406 modulating agent, an antisense 22406 nucleic acid molecule, a 22406-specific antibody, or a 22406-binding partner) in an appropriate animal model to determine the efficacy, toxicity, side effects, or mechanism of action, of treatment with such an agent. Furthermore, novel agents identified by the above-described screening assays can be used for treatments as described herein.

Detection Assays

Portions or fragments of the nucleic acid sequences identified herein can be used as polynucleotide reagents. For example, these sequences can be used to: (i) map their respective genes on a chromosome e.g., to locate gene regions associated with genetic disease or to associate 22406 with a disease; (ii) identify an individual from a minute biological sample (tissue typing); and (iii) aid in forensic identification of a biological sample. These applications are described in the subsections below.

Chromosome Mapping

The 22406 nucleotide sequences or portions thereof can be used to map the location of the 22406 genes on a chromosome. This process is called chromosome mapping. Chromosome mapping is useful in correlating the 22406 sequences with genes associated with disease.

Briefly, 22406 genes can be mapped to chromosomes by preparing PCR primers (preferably 15–25 bp in length) from the 22406 nucleotide sequences. These primers can then be used for PCR screening of somatic cell hybrids containing individual human chromosomes. Only those hybrids containing the human gene corresponding to the 22406 sequences will yield an amplified fragment.

A panel of somatic cell hybrids in which each cell line contains either a single human chromosome or a small number of human chromosomes, and a full set of mouse chromosomes, can allow easy mapping of individual genes to specific human chromosomes. (D'Eustachio et al. (1983) *Science* 220:919–924). Other mapping strategies e.g., in situ hybridization (described in Fan et al. (1990) *Proc. Natl. Acad. Sci. USA* 87:6223–27), pre-screening with labeled flow-sorted chromosomes, and pre-selection by hybridization to chromosome specific cDNA libraries can be used to map 22406 to a chromosomal location.

Fluorescence in situ hybridization (FISH) of a DNA sequence to a metaphase chromosomal spread can further be used to provide a precise chromosomal location in one step. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al. *Human Chromosomes: A Manual of Basic Techniques* (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland et al. (1987) *Nature* 325:783–787.

Moreover, differences in the DNA sequences between individuals affected and unaffected with a disease associated with the 22406 gene, can be determnined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing 22406 sequences can be used to identify individuals from biological samples using, e.g., restriction fragment length polymorphism (RFLP). In this technique, an individual's genomic DNA is digested with one or more restriction enzymes, the fragments separated, e.g., in a Southern blot, and probed to yield bands for identification. The sequences of the present invention are useful as additional DNA markers for RFLP (described in U.S. Pat. No. 5,272,057).

Furthermore, the sequences of the present invention can also be used to determine the actual base-by-base DNA sequence of selected portions of an individual's genome. Thus, the 22406 nucleotide sequences described herein can be used to prepare two PCR primers from the 5' and 3' ends of the sequences. These primers can then be used to amplify an individual's DNA and subsequently sequence it. Panels of corresponding DNA sequences from individuals, prepared in this manner, can provide unique individual identifications, as each individual will have a unique set of such DNA sequences due to allelic differences.

Allelic variation occurs to some degree in the coding regions of these sequences, and to a greater degree in the noncoding regions. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 can provide positive individual identification with a panel of perhaps 10 to 1,000 primers which each yield a noncoding amplified sequence of 100 bases. If predicted coding sequences, such as those in SEQ ID NO:3 are used, a more appropriate number of primers for positive individual identification would be 500–2,000.

If a panel of reagents from 22406 nucleotide sequences described herein is used to generate a unique identification database for an individual, those same reagents can later be used to identify tissue from that individual. Using the unique identification database, positive identification of the individual, living or dead, can be made from extremely small tissue samples.

Use of Partial 22406 Sequences in Forensic Biology

DNA-based identification techniques can also be used in forensic biology. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 (e.g., fragments derived from the noncoding regions of SEQ ID NO:1 having a length of at least 20 bases, preferably at least 30 bases) are particularly appropriate for this use.

The 22406 nucleotide sequences described herein can further be used to provide polynucleotide reagents, e.g., labeled or labelable probes which can be used in, for example, an in situ hybridization technique, to identify a specific tissue, e.g., a tissue containing pyridoxal-phosphate dependent serine racemase activity. This can be very useful in cases where a forensic pathologist is presented with a tissue of unknown origin. Panels of such 22406 probes can be used to identify tissue by species and/or by organ type.

In a similar fashion, these reagents, e.g., 22406 primers or probes can be used to screen tissue culture for contamination (i.e. screen for the presence of a mixture of different types of cells in a culture).

Predictive Medicine

The present invention also pertains to the field of predictive medicine in which diagnostic assays, prognostic assays, and monitoring clinical trials are used for prognostic (predictive) purposes to thereby treat an individual.

Generally, the invention provides, a method of determining if a subject is at risk for a disorder related to a lesion in or the misexpression of a gene which encodes 22406.

Such disorders include, e.g., a disorder associated with the misexpression of 22406, or a neurological disorder.

The method includes one or more of the following:

detecting, in a tissue of the subject, the presence or absence of a mutation which affects the expression of the 22406 gene, or detecting the presence or absence of a mutation in a region which controls the expression of the gene, e.g., a mutation in the 5' control region;

detecting, in a tissue of the subject, the presence or absence of a mutation which alters the structure of the 22406 gene;

detecting, in a tissue of the subject, the misexpression of the 22406 gene, at the mRNA level, e.g., detecting a non-wild type level of a mRNA;

detecting, in a tissue of the subject, the misexpression of the gene, at the protein level, e.g., detecting a non-wild type level of a 22406 polypeptide.

In preferred embodiments the method includes: ascertaining the existence of at least one of: a deletion of one or more nucleotides from the 22406 gene; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from SEQ ID NO:1 naturally occurring mutants thereof or 5' or 3' flanking sequences naturally associated with the 22406 gene; (ii) exposing the probe/primer to nucleic acid of the tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of the 22406 gene; the presence of a non-wild type splicing pattern of a messenger RNA transcript of the gene; or a non-wild type level of 22406.

Methods of the invention can be used prenatally or to determine if a subject's offspring will be at risk for a disorder.

In preferred embodiments the method includes determining the structure of a 22406 gene, an abnormal structure being indicative of risk for the disorder.

In preferred embodiments the method includes contacting a sample form the subject with an antibody to the 22406 protein or a nucleic acid, which hybridizes specifically with the gene. These and other embodiments are discussed below.

Diagnostic and Prognostic Assays

The presence, level, or absence of 22406 protein or nucleic acid in a biological sample can be evaluated by obtaining a biological sample from a test subject and contacting the biological sample with a compound or an agent capable of detecting 22406 protein or nucleic acid (e.g., mRNA, genomic DNA) that encodes 22406 protein such that, the presence of 22406 protein or nucleic acid is detected in the biological sample. The term "biological sample" includes tissues, cells and biological fluids isolated from a subject, as well as tissues, cells and fluids present within a subject. A preferred biological sample is serum. The level of expression of the 22406 gene can be measured in a number of ways, including, but not limited to: measuring the mRNA encoded by the 22406 genes; measuring the amount of protein encoded by the 22406 genes; or measuring the activity of the protein encoded by the 22406 genes.

The level of mRNA corresponding to the 22406 gene in a cell can be determined both by in situ and by in vitro formats.

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length 22406 nucleic acid, such as the nucleic acid of SEQ ID NO:1, or a portion thereof, such as an oligonucleotide of at least 7, 15, 20, 25, 30, 35, 40, 45, 50, 100, 250 or 500 nucleotides in length and sufficient to specifically hybridize under stringent conditions to 22406 mRNA or genomic DNA. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by the 22406 genes.

The level of mRNA in a sample that is encoded by one of 22406 can be evaluated with nucleic acid amplification, e.g., by rtPCR (Mullis, 1987, U.S. Pat. No. 4,683,202), ligase chain reaction (Barany (1991) *Proc. Natl. Acad. Sci. USA* 88:189–193), self sustained sequence replication (Guatelli etal. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), rolling circle replication (Lizardi et al. U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the 22406 gene being analyzed.

In another embodiment, the methods further contacting a control sample with a compound or agent capable of detecting 22406 mRNA, or genomic DNA, and comparing the presence of 22406 mRNA or genomic DNA in the control sample with the presence of 22406 mRNA or genomic DNA in the test sample.

A variety of methods can be used to determine the level of protein encoded by 22406. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')$_2$) can be used. The termn "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect 22406 protein in a biological sample in vitro as well as in vivo. In vitro techniques for detection of 22406 protein include enzyme linked immunosorbent assays (ELISAs), immunoprecipitations, immunofluorescence, enzyme immunoassay (EIA), radioimmunoassay (RIA), and Western blot analysis. In vivo techniques for detection of 22406 protein include introducing into a subject a labeled anti-22406 antibody. For example, the antibody can be labeled with a radioactive marker whose presence and location in a subject can be detected by standard imaging techniques.

In another embodiment, the methods further include contacting the control sample with a compound or agent capable of detecting 22406 protein, and comparing the presence of 22406 protein in the control sample with the presence of 22406 protein in the test sample.

The invention also includes kits for detecting the presence of 22406 in a biological sample. For example, the kit can include a compound or agent capable of detecting 22406 protein or mRNA in a biological sample; and a standard. The compound or agent can be packaged in a suitable container. The kit can further comprise instructions for using the kit to detect 22406 protein or nucleic acid.

For antibody-based kits, the kit can include: (1) a first antibody (e.g., attached to a solid support) which binds to a polypeptide corresponding to a marker of the invention; and, optionally, (2) a second, different antibody which binds to either the polypeptide or the first antibody and is conjugated to a detectable agent.

For oligonucleotide-based kits, the kit can include: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also includes a buffering agent, a preservative, or a protein-stabilizing agent. The kit can also includes components necessary for detecting the detectable agent (e.g., an enzyme or a substrate). The kit can also contain a control sample or a series of control samples which can be assayed and compared to the test sample contained. Each component of the kit can be enclosed within an individual container and all of the various containers can be within a single package, along with instructions for interpreting the results of the assays performed using the kit.

The diagnostic methods described herein can identify subjects having, or at risk of developing, a disease or disorder associated with misexpressed or aberrant or unwanted 22406 expression or activity. As used herein, the term "unwanted" includes an unwanted phenomenon involved in a biological response such as neurodegeneration.

In one embodiment, a disease or disorder associated with aberrant or unwanted 22406 expression or activity is identified. A test sample is obtained from a subject and 22406 protein or nucleic acid (e.g., mRNA or genomic DNA) is evaluated, wherein the level, e.g., the presence or absence, of 22406 protein or nucleic acid is diagnostic for a subject having or at risk of developing a disease or disorder associated with aberrant or unwanted 22406 expression or activity. As used herein, a "test sample" refers to a biological sample obtained from a subject of interest, including a biological fluid (e.g., serum), cell sample, or tissue.

The prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant or unwanted 22406 expression or activity. For example, such methods can be used to determine whether a subject can be effectively treated with an agent for a neurodegenerative disorder.

The methods of the invention can also be used to detect genetic alterations in a 22406 gene, thereby determining if a subject with the altered gene is at risk for a disorder characterized by misregulation in 22406 protein activity or nucleic acid expression, such as a neurodegenerative disorder. In preferred embodiments, the methods include detecting, in a sample from the subject, the presence or absence of a genetic alteration characterized by at least one of an alteration affecting the integrity of a gene encoding a 22406-protein, or the misexpression of the 22406 gene. For example, such genetic alterations can be detected by ascertaining the existence of at least one of 1) a deletion of one or more nucleotides from a 22406 gene; 2) an addition of one or more nucleotides to a 22406 gene; 3) a substitution of one or more nucleotides of a 22406 gene, 4) a chromosomal rearrangement of a 22406 gene; 5) an alteration in the level of a messenger RNA transcript of a 22406 gene, 6) aberrant modification of a 22406 gene, such as of the methylation pattern of the genomic DNA, 7) the presence of a non-wild type splicing. pattern of a messenger RNA transcript of a 22406 gene, 8) a non-wild type level of a 22406-protein, 9) allelic loss of a 22406 gene, and 10) inappropriate post-translational modification of a 22406-protein.

An alteration can be detected without a probe/primer in a polymerase chain reaction, such as anchor PCR or RACE PCR, or, alternatively, in a ligation chain reaction (LCR), the latter of which can be particularly useful for detecting point mutations in the 22406-gene. This method can include the steps of collecting a sample of cells from a subject, isolating nucleic acid (e.g., genomic, mRNA or both) from the sample, contacting the nucleic acid sample with one or more primers which specifically hybridize to a 22406 gene under conditions such that hybridization and amplification of the 22406-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio-Technology* 6:1197), or other nucleic acid amplification methods, followed by the detection of the amplified molecules using techniques known to those of skill in the art.

In another embodiment, mutations in a 22406 gene from a sample cell can be identified by detecting alterations in restriction enzyme cleavage patterns. For example, sample and control DNA is isolated, amplified (optionally), digested with one or more restriction endonucleases, and fragment length sizes are determined, e.g., by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in 22406 can be identified by hybridizing a sample and control nucleic acids, e.g., DNA or RNA, two-dimensional arrays, e.g., chip based arrays. Such arrays include a plurality of addresses, each of which is positionally distinguishable from the other. A different probe is located at each address of the plurality. The arrays can have a high density of addresses, e.g., can contain hundreds or thousands of oligonucleotides probes (Cronin et al. (1996) *Human Mutation* 7: 244–255; Kozal et al. (1996) *Nature Medicine* 2:753–759). For example, genetic mutations in 22406 can be identified in two dimensional arrays containing light-generated DNA probes as described in Cronin et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the 22406 gene and detect mutations by comparing the sequence of the sample 22406 with the corresponding wild-type (control) sequence. Automated sequencing procedures can be utilized when performing the diagnostic assays (Naeve et al.(1995) *Biotechniques* 19:448–453), including sequencing by mass spectrometry.

Other methods for detecting mutations in the 22406 gene include methods in which protection from cleavage agents is used to detect mismatched bases in RNA/RNA or RNA/DNA heteroduplexes (Myers et al. (1985) *Science* 230:1242–1246; Cotton et al. (1988) *Proc. Natl. Acad. Sci. USA* 85:4397–4401; Saleeba et al. (1992) *Methods Enzymol.* 217:286–295).

In still another embodiment, the mismatch cleavage reaction employs one or more proteins that recognize mismatched base pairs in double-stranded DNA (so called "DNA mismatch repair" enzymes) in defined systems for detecting and mapping point mutations in 22406 cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657–1662; U.S. Pat. No. 5,459,039).

In other embodiments, alterations in electrophoretic mobility will be used to identify mutations in 22406 genes. For example, single strand conformation polymorphism (SSCP) may be used to detect differences in electrophoretic mobility between mutant and wild type nucleic acids (Orita et al. (1989) *Proc. Natl. Acad. Sci. USA*: 86:2766–2770, see also Cotton (1993) *Mutat. Res.* 285:125–144; and Hayashi (1992) *Genet. Anal. Tech. Appl.* 9:73–79). Single-stranded DNA fragments of sample and control 22406 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495–498). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension (Saiki et al. (1986) *Nature* 324:163); Saiki et al. (1989) *Proc. Natl. Acad. Sci. USA* 86:6230).

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437–2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1–7). It is anticipated that in certain embodiments amplification may also be performed using Taq ligase for amplification (Barany (1991) *Proc. Natl. Acad. Sci USA* 88:189–193). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving a 22406 gene.

Use of 22406 Molecules as Surrogate Markers

The 22406 molecules of the invention are also useful as markers of disorders or disease states, as markers for precursors of disease states, as markers for predisposition of disease states, as markers of drug activity, or as markers of the pharmacogenomic profile of a subject. Using the methods described herein, the presence, absence and/or quantity of the 22406 molecules of the invention may be detected, and may be correlated with one or more biological states in vivo. For example, the 22406 molecules of the invention may serve as surrogate markers for one or more disorders or disease states or for conditions leading up to disease states. As used herein, a "surrogate marker" is an objective biochemical marker which correlates with the absence or presence of a disease or disorder, or with the progression of a disease or disorder (e.g., with the presence or absence of a tumor). The presence or quantity of such markers is independent of the disease. Therefore, these markers may serve to indicate whether a particular course of treatment is effective in lessening a disease state or disorder. Surrogate markers are of particular use when the presence or extent of a disease state or disorder is difficult to assess through standard methodologies (e.g., early stage tumors), or when an assessment of disease progression is desired before a potentially dangerous clinical endpoint is reached (e.g., an assessment of cardiovascular disease may be made using cholesterol levels as a surrogate marker, and an analysis of HIV infection may be made using HIV RNA levels as a surrogate marker, well in advance of the undesirable clinical outcomes of myocardial infarction or fully-developed AIDS). Examples of the use of surrogate markers in the art include: Koomen et al. (2000) *J. Mass. Spectrom.* 35: 258–264; and James (1994) *AIDS Treatment News Archive* 209.

The 22406 molecules of the invention are also useful as pharmacodynamic markers. As used herein, a "pharmacodynamic marker" is an objective biochemical marker which correlates specifically with drug effects. The presence or quantity of a pharmacodynamic marker is not related to the disease state or disorder for which the drug is being administered; therefore, the presence or quantity of the marker is indicative of the presence or activity of the drug in a subject. For example, a pharmacodynamic marker may be indicative of the concentration of the drug in a biological tissue, in that the marker is either expressed or transcribed or not expressed or transcribed in that tissue in relationship to the level of the drug. In this fashion, the distribution or uptake of the drug may be monitored by the pharmacodynamic marker. Similarly, the presence or quantity of the pharmacodynamic marker may be related to the presence or quantity of the metabolic product of a drug, such that the presence or quantity of the marker is indicative of the relative breakdown rate of the drug in vivo. Pharmacodynamic markers are of particular use in increasing the sensitivity of detection of drug effects, particularly when the drug is administered in low doses. Since even a small amount of a drug may be sufficient to activate multiple rounds of marker (e.g., a 22406 marker) transcription or expression, the amplified marker may be in a quantity which is more readily detectable than the drug itself. Also, the marker may be more easily detected due to the nature of the marker itself; for example, using the methods described herein, anti-22406 antibodies may be employed in an immune-based detection system for a 22406 protein marker, or 22406-specific radiolabeled probes may be used to detect a 22406 mRNA marker. Furthermore, the use of a pharmacodynamic marker may offer mechanism-based prediction of risk due to drug treatment beyond the range of possible direct observations. Examples of the use of pharmacodynamic markers in the art include: Matsuda et al. U.S. Pat. No. 6,033,862; Hattis et al. (1991) *Env. Health Perspect.* 90:229–238; Schentag (1999) *Am. J. Health-Syst. Pharm.* 56 *Suppl.*3:S21–S24; and Nicolau (1999) *Am, J. Health-Syst. Pharm.* 56 *Suppl.*3:S 16–S20.

The 22406 molecules of the invention are also useful as pharmacogenomic markers. As used herein, a "pharmacogenomic marker" is an objective biochemical marker which correlates with a specific clinical drug response or susceptibility in a subject (see, e.g., McLeod et al. (1999) *Eur. J. Cancer* 35(12): 1650–1652). The presence or quantity of the pharmacogenomic marker is related to the predicted response of the subject to a specific drug or class of drugs prior to administration of the drug. By assessing the presence or quantity of one or more pharmacogenomic markers in a subject, a drug therapy which is most appropriate for the subject, or which is predicted to have a greater degree of success, may be selected. For example, based on the presence or quantity of RNA, or protein (e.g., 22406 protein or RNA) in a subject, a drug or course of treatment may be selected that is optimized for the treatment of the specific neurological disorder likely to be affecting the subject. Similarly, the presence or absence of a specific sequence mutation in 22406 DNA may correlate 22406 drug response. The use of pharmacogenomic markers therefore permits the application of the most appropriate treatment for each subject without having to administer the therapy.

Pharmaceutical Compositions

The nucleic acid and polypeptides, fragments thereof, as well as anti-22406 antibodies (also referred to herein as "active compounds") of the invention can be incorporated into pharmaceutical compositions. Such compositions typically include the nucleic acid molecule, protein, or antibody and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intraderrnal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be. permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery, In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, preferably between 2 to 8 weeks, more preferably between about 3 to 7 weeks, and even more preferably for about 4, 5, or 6 weeks. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments.

For antibodies, the preferred dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the brain). A method for lipidation of antibodies is described by Cruikshank et al. ((1997) *J. Acquired Immune Deficiency Syndromes and Human Retrovirology* 14:193).

The present invention encompasses agents which modulate expression or activity. An agent may, for example, be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, .glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Alternatively, an antibody can be conjugated to a second antibody to form an antibody heteroconjugate as described by Segal in U.S. Pat. No. 4,676,980.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

The present invention provides for both prophylactic and therapeutic methods of treating a subject at risk of (or susceptible to) a disorder or having a disorder associated with aberrant or unwanted 22406 expression or activity. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype".) Thus, another aspect of the invention provides methods for tailoring an individual's prophylactic or therapeutic treatment with either the 22406 molecules of the present invention or 22406 modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, a disease or condition associated with an aberrant or unwanted 22406 expression or activity, by administering to the subject a 22406 or an agent which modulates 22406 expression or at least one 22406 activity. Subjects at risk for a disease which is caused or contributed to by aberrant or unwanted 22406 expression or activity can be identified by, for example, any or a combination of diagnostic or prognostic assays as described herein. Administration of a prophylactic agent can occur prior to the manifestation of symptoms characteristic of the 22406 aberrance, such that a disease or disorder is prevented or, alternatively, delayed in its progression. Depending on the type of 22406 aberrance, for example, a 22406, 22406 agonist or 22406 antagonist agent can be used for treating the subject. The appropriate agent can be determined based on screening assays described herein.

It is possible that some 22406 disorders can be caused, at least in part, by an abnormal level of gene product, or by the presence of a gene product exhibiting abnormal activity. As such, the reduction in the level and/or activity of such gene products would bring about the amelioration of disorder symptoms.

As discussed, successful treatment of 22406 disorders can be brought about by techniques that serve to inhibit the expression or activity of target gene products. For example, compounds, e.g., an agent identified using an assays described above, that proves to exhibit negative modulatory activity, can be used in accordance with the invention to prevent and/or ameliorate symptoms of 22406 disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, scFV molecules, and epitope-binding fragments thereof).

Further, antisense and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via gene therapy method. Alternatively, in instances in that the target gene encodes an extracellular protein, it can be preferable to co-administer normal target gene protein into the cell or tissue in order to maintain the requisite level of cellular or tissue target gene activity.

Another method by which nucleic acid molecules may be utilized in treating or preventing a disease characterized by 22406 expression is through the use of aptamer molecules specific for 22406 protein. Aptamers are nucleic acid molecules having a tertiary structure which permits them to specifically bind to protein ligands (see, e.g., Osborne, et al. (1997) *Curr. Opin. Chiem. Biol.* 1(1):5–9; and Patel (1997 June) *Curr. Opin. Chiem. Biol.* 1(1):32–46). Since nucleic acid molecules may in many cases be more conveniently introduced into target cells than therapeutic protein molecules may be, aptamers offer a method by which 22406 protein activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of 22406 disorders. For a description of antibodies, see the Antibody section above.

In circumstances wherein injection of an animal or a human subject with a 22406 protein or epitope for stimulating antibody production is harmful to the subject, it is possible to generate an immune response against 22406 through the use of anti-idiotypic antibodies (see, for example, Herlyn (1999) *Ann. Med.* 31(1):66–78; and Bhattacharya-Chatterjee et al. (1998) *Cancer Treat. Res.* 94:51–68). If an anti-idiotypic antibody is introduced into a mammal or human subject, it should stimulate the production of anti-anti-idiotypic antibodies, which should be specific to the 22406 protein. Vaccines directed to a disease characterized by 22406 expression may also be generated in this fashion.

In instances where the target antigen is intracellular and whole antibodies are used, internalizing antibodies may be preferred. Lipofectin or liposomes can be used to deliver the antibody or a fragment of the Fab region that binds to the target antigen into cells. Where fragments of the antibody are used, the smallest inhibitory fragment that binds to the target antigen is preferred. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population (see e.g., Marasco et al. (1993) *Proc. Natl. Acad. Sci. USA* 90:7889–7893).

The identified compounds that inhibit target gene expression, synthesis and/or activity can be administered to a patient at therapeutically effective doses to prevent, treat or ameliorate 22406 disorders. A therapeutically effective dose refers to that amount of the compound sufficient to result in amelioration of symptoms of the disorders.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound which is able to modulate 22406 activity is used as a template, or "imprinting molecule", to spatially organize polymerizable monomers prior to their polymerization with catalytic reagents. The subsequent removal of the imprinted molecule leaves a polymer matrix which contains a repeated "negative image" of the compound and is able to selectively rebind the molecule under biological assay conditions. A detailed review of this technique can be seen in Ansell et al. (1996) *Current Opinion in Biotechnology* 7:89–94 and in Shea (1994) *Trends in Polymer Science* 2:166–173. Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al. (1993) *Nature* 361:645–647. Through the use of isotope-labeling, the "free" concentration of compound which modulates the expression or activity of 22406 can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz et al. (1995) *Analytical Chemistry* 67:2142–2144.

Another aspect of the invention pertains to methods of modulating 22406 expression or activity for therapeutic purposes. Accordingly, in an exemplary embodiment, the modulatory method of the invention involves contacting a cell with a 22406 or agent that modulates one or more of the activities of 22406 protein activity associated with the cell. An agent that modulates 22406 protein activity can be an agent as described herein, such as a nucleic acid or a protein, a naturally-occurring target molecule of a 22406 protein (e.g., a 22406 substrate or receptor), a 22406 antibody, a 22406 agonist or antagonist, a peptidomimetic of a 22406 agonist or antagonist, or other small molecule.

In one embodiment, the agent stimulates one or more 22406 activities. Examples of such stimulatory agents include active 22406 protein and a nucleic acid molecule encoding 22406. In another embodiment, the agent inhibits one or more 22406 activities. Examples of such inhibitory agents include antisense 22406 nucleic acid molecules, anti-22406 antibodies, and 22406 inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant or unwanted expression or activity of a 22406 protein or nucleic acid molecule. In one embodiment, the method involves administering an agent (e.g., an agent identified by a screening assay described herein), or combination of agents that modulates (e.g., upregulates or downregulates) 22406 expression or activity. In another embodiment, the method involves administering a 22406 protein or nucleic acid molecule as therapy to compensate for reduced, aberrant, or unwanted 22406 expression or activity.

Stimulation of 22406 activity is desirable in situations in which 22406 is abnormally downregulated and/or in which increased 22406 activity is likely to have a beneficial effect.

For example, stimulation of 22406 activity is desirable in situations in which a 22406 is downregulated and/or in which increased 22406 activity is likely to have a beneficial effect. Likewise, inhibition of 22406 activity is desirable in situations in which 22406 is abnormally upregulated and/or in which decreased 22406 activity is likely to have a beneficial effect.

The 22406 molecules can act as novel diagnostic targets and therapeutic agents for controlling one or more of brain disorders, including but not limited to, behavioral changes associated with learning, memory, convulsion, anxiety, psychotomimetic induced abnormal behavior, cerebellar ataxia, and neurodengeneration. Inhibitors of 22406 protein can be expected to quell anxiety and epilepsy and to prevent damage from stroke and certain neurodegenerative conditions including Alzheimer's disease. On the other hand, stimulating 22406 protein might improve schizophrenia symptoms, which are partly caused by depressed NMDA receptor function. In addition, 22406 protein can be expected to be involved in various disorders of the tissues in which it is expressed, including heart disorders, liver disorders, prostrate disorders, skeletal muscle disorders, dermal fibroblast disorders, and blood vessel disorders. All of the disorders described supra are disorders that may be treated or diagnosed by methods described herein.

Pharmacogenomics

The 22406 molecules of the present invention, as well as agents, or modulators which have a stimulatory or inhibitory effect on 22406 activity (e.g., 22406 gene expression) as identified by a screening assay described herein can be administered to individuals to treat (prophylactically or therapeutically) 22406 associated disorders (e.g., neurological disorders) associated with aberrant or unwanted 22406 activity. In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a 22406 molecule or 22406 modulator as well as tailorin, the dosage andlor therapeutic regimen of treatment with a 22406 molecule or 22406 modulator.

Phairnacogenomics deals with clinically significant hereditary variations in the response to drugs due to altered drug disposition and abnormal action in affected persons. See, for example, Eichelbaum et al. (1996) *Clin. Exp. Pharmacol. Physiol.* 23(10–11): 983–985 and Linder et al. (1997) *Clin. Chem.* 43(2):254–266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000–100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high-resolution map can be generated from a combination of some ten million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drug's target is known (e.g., a 22406 protein of the present invention), all common variants of that gene can be fairly easily identified in the population and it can be determined if having one version of the gene versus another is associated with a particular drug response.

Alternatively, a method termed the "gene expression profiling", can be utilized to identify genes that predict drug response. For example, the gene expression of an animal dosed with a drug (e.g., a 22406 molecule or 22406 modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a subject with a 22406 molecule or 22406 modulator, such as a modulator identified by one of the exemplary screening assays described herein.

The present invention further provides methods for identifying new agents, or combinations, that are based on identifying agents that modulate the activity of one or more of the gene products encoded by one or more of the 22406 genes of the present invention, wherein these products may be associated with resistance of the cells to a therapeutic agent. Specifically, the activity of the proteins encoded by the 22406 genes of the present invention can be used as a basis for identifying agents for overcoming agent resistance. By blocking the activity of one or more of the resistance proteins, target cells, e.g., brain cells, will become sensitive to treatment with an agent that the unmodified target cells were resistant to.

Monitoring the influence of agents (e.g., drugs) on the expression or activity of a 22406 protein can be applied in clinical trials. For example, the effectiveness of an agent determined by a screening assay as described herein to increase 22406 gene expression, protein levels, or upregulate 22406 activity, can be monitored in clinical trials of subjects exhibiting decreased 22406 gene expression, protein levels, or downregulated 22406 activity. Alternatively, the effectiveness of an agent determined by a screening assay to decrease 22406 gene expression, protein levels, or dowaregulate 22406 activity, can be monitored in clinical trials of subjects exhibiting increased 22406 gene expression, protein levels, or upregulated 22406 activity. In such clinical trials, the expression or activity of a 22406 gene, and preferably, other genes that have been implicated in, for example, a 22406-associated disorder can be used as a "read out" or markers of the phenotype of a particular cell.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, Eand each address of the plurality having a unique capture probe, e.g., a nucleic acid or peptide sequence; contacting the array with a 22406, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 22406 nucleic acid, polypeptide, or antibody.

The capture probes can be a set of nucleic acids from a selected sample, e.g., a sample of nucleic acids derived from a control or non-stimulated tissue or cell.

The method can include contacting the 22406 nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 22406. Such methods can be used to diagnose a subject, e.g., to evaluate risk for a disease or disorder, to evaluate suitability of a selected treatment for a subject, to evaluate whether a subject has a disease or disorder. 22406 is associated with pyridoxal-phosphate dependent serine racemase activity, thus it is useful for disorders associated with the brain.

The method can be used to detect SNPs, as described above.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 22406 or from a cell or subject in which a 22406 mediated response has been elicited, e.g., by contact of the cell with 22406 nucleic acid or protein, or administration to the cell or subject 22406 nucleic acid or protein; contacting the array with one or more inquiry probe, wherein an inquiry probe can be a nucleic acid, polypeptide, or antibody (which is preferably other than 22406 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 22406 (or does not express as highly as in the case of the 22406 positive plurality of capture probes) or from a cell or subject which in which a 22406 mediated response has not been elicited (or has been elicited to a lesser extent than in the first sample); contacting the array with one or more inquiry probes (which is preferably other than a 22406 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 22406, e.g., analyzing structure, function, or relatedness to other nucleic acid or amino acid sequences. The method includes: providing a 22406 nucleic acid or amino acid sequence; comparing the 22406 sequence with one or more preferably a plurality of sequences from a collection of sequences, e.g., a nucleic acid or protein sequence database; to thereby analyze 22406.

Preferred databases include GenBank™. The method can include evaluating the sequence identity between a 22406 sequence and a database sequence. The method can be performed by accessing the database at a second site, e.g., over the internet.

In another aspect, the invention features, a set of oligonucleotides, useful, e.g., for identifying SNP's, or identifying specific alleles of 22406. The set includes a plurality of oligonucleotides, each of which has a different nucleotide at an interrogation position, e.g., an SNP or the site of a mutation. In a preferred embodiment, the oligonucleotides of the plurality identical in sequence with one another (except for differences in length). The oligonucleotides can be provided with different labels, such that an oligonucleotides which hybridizes to one allele provides a signal that is distinguishable from an oligonucleotides which hybridizes to a second allele.

This invention is further illustrated by the following examples which should not be construed as limiting. The contents of all references, patents and published patent applications cited throughout this application are incorporated herein by reference.

EXAMPLES

Example 1

Identification and Characterization of Human 22406 cDNAs

The human 22406 sequence (FIGS. 1A–B; SEQ ID NO:1), which is approximately 1770 nucleotides long including untranslated regions, contains a predicted methionine-initiated coding sequence of about 1020 nucleotides (nucleotides 69–1088 of SEQ ID NO:1; SEQ ID NO:3). The coding sequence encodes a 340 amino acid protein (SEQ ID NO:2).

Example 2

Tissue Distribution of 22406 mRNA

Expression levels of 42812 in various tissue and cell types were determined by quantitative RT-PCR (Reverse Transcriptase Polymerase Chain Reaction; Taqman®) brand PCR kit, Applied Biosystems) (FIG. 9). The quantitative RT-PCR reactions were performed according to the kit manufacturer's instructions.

Northern blot hybridizations with various RNA samples can be performed under standard conditions and washed under stringent conditions, i.e., 0.2×SSC at 65° C. A DNA probe corresponding to all or a portion of the 22406 cDNA (SEQ ID NO:1) can be used. The DNA was radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) can be probed in ExpressHyb hybridization solution (Clontech) and washed at high stringency according to manufacturer's recommendations.

FIGS. 5 and 9 show expression of the 22406 protein in various human tissues. In FIG. 9 the tissue types are as follows from left to right: Aorta/Normal, Fetal Heart/Normal, Heart/Normal, Heart/CHF, Vein/Normal, SMC/Aortic, Nerve/Normal, Spinal Cord/Normal, Brain Cord/Normal, Brain Cortex/Normal, Brain Hypothalmus/Normal, Glial Cells (Astrocytes), Glioblastoma, Breast/Normal, Breast/Tumor, Ovary/Normal, Ovary/Tumor, Pancreas/Normal, Prostate/Normal, Prostate/Tumor, Colon/Normal, Colon/Tumor, Colon/IBD, Kidney/Normal, Liver/Normal, Liver/Fibrosis, Fetal Liver/Normal, Lung/Normal, Lung/COPD, Spleen/Normal, Tonsil/Normal, Lymph Node/Normal, Thymus/Normal, Epithelial Cells (Prostate), Endothelial Cells (Aortic), Skeletal Muscle/Normal, Fibroblasts (Dermal), Skin/Normal, Adipose/Normal, Osteoblasts (Primary), Osteoblasts (Undiff), Osteoblasts (Diff), Osteoclasts, NTC.

Example 3
Recombinant Expression of 22406 in Bacterial Cells

In this example, 22406 is expressed as a recombinant glutathione-S-transferase (GST) fusion polypeptide in *E. coli* and the fusion polypeptide is isolated and characterized. Specifically, 22406 is fused to GST and this fusion polypeptide is expressed in *E. coli*, e.g., strain PEB 199. Expression of the GST-22406 fusion protein in PEB199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

Example 4
Expression of Recombinant 22406 Protein in COS Cells

To express the 22406 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 22406 protein and an HA tag (Wilson et al (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 22406 DNA sequence is amplified by PCR using two primers. The 5' primer contains the restriction site of interest followed by approximately twenty nucleotides of the 22406 coding sequence starting from the initiation codon; the 3' end sequence contains complementary sequences to the other restriction site of interest, a translation stop codon, the HA tag or FLAG tag and the last 20 nucleotides of the 22406 coding sequence. The PCR amplified fragment and the pcDNA/Amp vector are digested with the appropriate restriction enzymes and the vector is dephosphorylated using the CIAP enzyme (New England Biolabs, Beverly, Mass.). Preferably the two restriction sites chosen are different so that the 22406 gene is inserted in the correct orientation. The ligation mixture is transformed into *E. coli* cells (strains HB101, DH5α, SURE, available from Stratagene Cloning Systems, La Jolla, Calif., can be used), the transformned culture is plated on ampicillin media plates, and resistant colonies are selected. Plasmid DNA is isolated from transformants and examined by restriction analysis for the presence of the correct fragment.

COS cells are subsequently transfected with the 22406-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook et al., *Molecular Cloning: A Laboratory Manual*. 2nd, ed., Cold Spring Harbor Laboratory, Cold Spring Harbor Laboratory Press, Cold Spring Harbor, NY, 1989. The expression of the 22406 polypeptide is detected by radiolabelling ($^{35}$S-methionine or $^{35}$S-cysteine available from NEN, Boston, Mass., can be used) and immunoprecipitation (Harlow et al., *Antibodies: A Laboratory Manual*, Cold Spring Harbor Laboratory Press, Cold Spring Harbor, NY, 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 22406 coding sequence is cloned directly into the polylinker of the pcDNA/Amp vector using the appropriate restriction sites. The resulting plasmid is transfected into COS cells in the manner described above, and the expression of the 22406 polypeptide is detected by radiolabelling and immunoprecipitation using a 22406 specific monoclonal antibody.

Equivalents

Those skilled in the art will recognize, or be able to ascertain using no more than routine experimentation, many equivalents to the specific embodiments of the invention described herein. Such equivalents are intended to be encompassed by the following claims.

That which is claimed:

1. An isolated nucleic acid molecule selected from the group consisting of:
   a) a nucleic acid molecule comprising a nucleotide sequence which is at least 95% identical to the full length of the nucleotide sequence of SEQ ID NO: 1 or SEQ ID NO: 3, wherein said nucleic acid molecule encodes a polypeptide having pyridoxal-phosphate dependent serine racemase activity; and
   b) a nucleic acid molecule comprising a nucleotide sequence which encodes a polypeptide comprising the; amino acid sequence of SEQ ID NO: 2, wherein said polypeptide has pyridoxal-phosphate dependent serine racemase activity.

2. The isolated nucleic acid molecule of claim 1, which is selected from the group consisting of:
   a) a nucleic acid comprising the nucleotide sequence of SEQ ID NO:1 or SEQ ID NO:3; and
   b) a nucleic acid molecule which encodes a polypeptide comprising the amino acid sequence of SEQ ID NO:2.

3. The nucleic acid molecule of claim 1 further comprising vector nucleic acid sequences.

4. The nucleic acid molecule of claim 1 further comprising nucleic acid sequences encoding a heterologous polypeptide.

5. A host cell which contains the nucleic acid molecule of claim 1.

6. The host cell of claim 5 which is a mammalian host cell.

7. A non-human mammalian host cell containing the nucleic acid molecule of claim 1.

8. A method for producing a polypeptide comprising the amino acid sequence of SEQ ID NO: 2; comprising culturing the host cell of claim 5 under conditions in which the nucleic acid molecule is expressed.

* * * * *